(12) United States Patent
Zenhausern et al.

(10) Patent No.: US 11,221,966 B2
(45) Date of Patent: Jan. 11, 2022

(54) METHOD AND SYSTEM FOR BIOLOGICAL INFORMATION PATTERN STORAGE AND READOUT

(71) Applicants: Arizona Board of Regents on Behalf of the University of Arizona, Tucson, AZ (US); Whitespace Enterprise Corporation, Tempe, AZ (US)

(72) Inventors: Frederic Zenhausern, Phoenix, AZ (US); Cedric Hurth, Castelldefels (ES)

(73) Assignees: Arizona Board of Regents on Behalf of The University of Arizona, Tucson, AZ (US); Whitespace Enterprise Corporation, Tempe, AZ (US)

( * ) Notice: Subject to any disclaimer, the term of this patent is extended or adjusted under 35 U.S.C. 154(b) by 195 days.

(21) Appl. No.: 16/431,329

(22) Filed: Jun. 4, 2019

(65) Prior Publication Data

US 2019/0370188 A1    Dec. 5, 2019

Related U.S. Application Data

(60) Provisional application No. 62/680,908, filed on Jun. 5, 2018.

(51) Int. Cl.
| | | |
|---|---|---|
| *G06F 12/123* | (2016.01) | |
| *G06F 16/242* | (2019.01) | |
| *G06F 16/38* | (2019.01) | |
| *C12Q 1/6844* | (2018.01) | |

(52) U.S. Cl.
CPC ......... *G06F 12/125* (2013.01); *C12Q 1/6844* (2013.01); *G06F 16/2445* (2019.01); *G06F 16/38* (2019.01)

(58) Field of Classification Search
CPC .. C12Q 1/6869; C12Q 1/6844; C12Q 1/6825; G06F 12/125; G06F 16/2445; G06F 16/38
USPC ........................ 711/103, 148, 158, E12.008; 707/999.102, E17.009, 915; 713/186; 435/6.1, 6.11
See application file for complete search history.

(56) References Cited

U.S. PATENT DOCUMENTS

| | | | |
|---|---|---|---|
| 6,015,714 A | 6/2000 | Baldarelli et al. | |
| 7,948,015 B2 | 5/2011 | Rothberg et al. | |
| 9,165,979 B2 * | 10/2015 | Tran .................... | G01N 27/122 |
| 2007/0072213 A1 * | 3/2007 | Perov ................... | G06T 7/0004 |
| | | | 435/6.11 |
| 2009/0227476 A1 | 9/2009 | Malcolm | |

(Continued)

OTHER PUBLICATIONS

Accardo et al. (2011) "Ultrahydrophobic PMMA micro- and nano-textured surfaces fabricated by optical lithography and plasma etching for X-ray diffraction studies," Microelectron. Eng. 88(8): 1660-1663.

(Continued)

*Primary Examiner* — Sanjiv Shah
*Assistant Examiner* — Edward Waddy, Jr.
(74) *Attorney, Agent, or Firm* — Leydig, Voit & Mayer, Ltd.

(57) ABSTRACT

Provided herein are biological information pattern (BIP) arrays and related methods for reading out information stored in a biological medium. In this manner, encoded digital information in biomolecular medium can be used as a high data density storage medium that may be read-out and accessed in a label-free manner.

14 Claims, 11 Drawing Sheets

Specification includes a Sequence Listing.

(56) References Cited

U.S. PATENT DOCUMENTS

| | | | | |
|---|---|---|---|---|
| 2010/0027118 | A1* | 2/2010 | Rosenman | G02B 26/005 |
| | | | | 359/507 |
| 2013/0011837 | A1* | 1/2013 | Dickinson | C12Q 1/6837 |
| | | | | 435/6.11 |
| 2017/0016063 | A1* | 1/2017 | McGall | C12Q 2535/122 |
| 2019/0355442 | A1* | 11/2019 | Merriman | G01N 27/3271 |

OTHER PUBLICATIONS

Baughman et al. (2010) "Evaporative Deposition Patterns of Bacteria from a Sessile Drop: Effect of Changes in Surface Wettability Due to Exposure to a Laboratory Atmosphere," Langmuir 26(10): 7293-7298.

Bhardwaj et al. (2010) "Self-Assembly of Colloidal Particles from Evaporating Droplets: Role of DLVO Interactions and Proposition of a Phase Diagram," Langmuir 26(11): 7833-7842.

Bornholt et al. (2016) "A DNA-Based Archival Storage System," ASPLOS '16, Apr. 2-6, 2016, Atlanta, GA, USA: 13 pp.

Church et al. (2012) "Next-Generation Digital Information Storage in DNA," Science 337(6102): 1628, 1 pp.

Dressman et al. (2003) "Transforming single DNA molecules into fluorescent magnetic particles for detection and enumeration of genetic variations," Proc. Nat. Acad. Sci. USA 100(15): 8817-8822.

Erlich et al. (Mar. 2017) "DNA Fountain enables a robust and efficient storage architecture," Science 355(6328): 950-954.

Forney et al. (1992) "Control of humidity in small controlled-environment chambers using glycerol-water solutions," HortTechnology 2(1): 52-54.

Goldman et al. (2013) "Toward practical high-capacity low-maintenance storage of digital information in synthesised DNA," Nature 494(7435): 77-80.

Holmberg et al. (2005) "The biotin-streptavidin interaction can be reversibly broken using water at elevated temperatures," Electrophoresis 26(3): 501-510.

Howley et al. (1979) "A rapid method for detecting and mapping homology between heterologous DNAs. Evaluation of polyomavirus genomes," J. Biol. Chem. 254(11): 4876-4883.

Hu et al. (2005) "Analysis of the Effects of Marangoni Stresses on the Microflow in an Evaporating Sessile Droplet," Langmuir 21 (9): 3972-3980.

Hurth et al. (2015) "Biomolecular interactions control the shape of stains from drying droplets of complex fluids," Chem. Eng. Sci. 137: 398-403.

Hurth et al. (Jun. 2018) "Influence of a single nucleotide polymorphism (SNP) and DNA hybridization on the drying patterns of micro droplets," Journal of Nanomedicine 2:1010, 1-8.

Kim et al. (2012) "Identification of fluid and substrate chemistry based on automatic pattern recognition of stains," Anal. Methods 4(1): 50-57.

Lee et al. (2012) "Water droplet evaporation on Cu-based hydrophobic surfaces with nano- and micro-structures," Int. J. Heat Mass Transf. 55(7-8): 2151-2159.

Lin et al. (2008) "Recent Patents and Advances in the Next-Generation Sequencing Technologies," Recent Pat Biomed Eng. 2008(1): 60-67.

Lin et al. (2015) "Emerging platforms using liquid biopsy to detect EGFR mutations in lung cancer," Expert Rev Mol Diagn. 15(11): 1427-1440.

Ristenpart et al. (2007) "Influence of Substrate Conductivity on Circulation Reversal in Evaporating Drops," Phys. Rev. Lett. 99(23): 234502-1-234502-4.

Sangani et al. (2009) "Capillary force on particles near a drop edge resting on a substrate and a criterion for contact line pinning," Phys. Rev. E 80: 011603-1-011603-15.

Sefiane et al. (2009) "Nanofluids droplets evaporation kinetics and wetting dynamics on rough heated substrates," Adv. Colloid Interface Sci. 147-148: 263-271.

Shipman et al. (Jul. 2017) "CRISPR-Cas encoding of a digital movie into the genomes of a population of living bacteria," Nature 547(7663): 345-349.

Takahashi et al. (Mar. 2019) "Demonstration of End-to-End Automation of DNA Data Storage," Scientific Reports 9: 4998, 1-5.

Thiele (2014) "Patterned deposition at moving contact lines," Adv. Colloid Interface Sci. 206: 399-413.

Trantum et al. (2012) "Biomarker-Mediated Disruption of Coffee-Ring Formation as a Low Resource Diagnostic Indicator," Langmuir 28(4): 2187-2193.

Wong et al. (1999) "Direct force measurements of the streptavidin-biotin interaction," Biomol. Eng. 16(1-4): 45-55.

Xu et al. (2011) "Evaporative self-assembly of nanowires on superhydrophobic surfaces of nanotip latching structures," Appl. Phys. Lett. 98(7): 073101-1-073101-3.

* cited by examiner

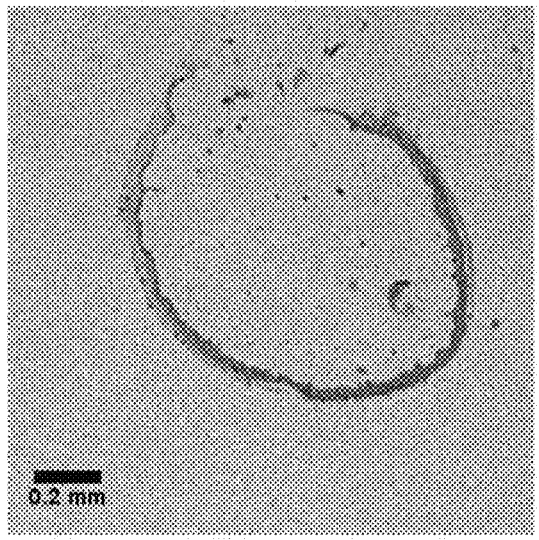
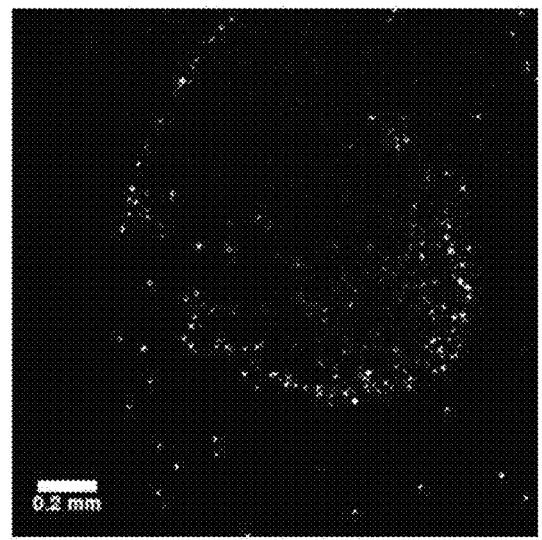
FIG. 7E    FIG. 7F
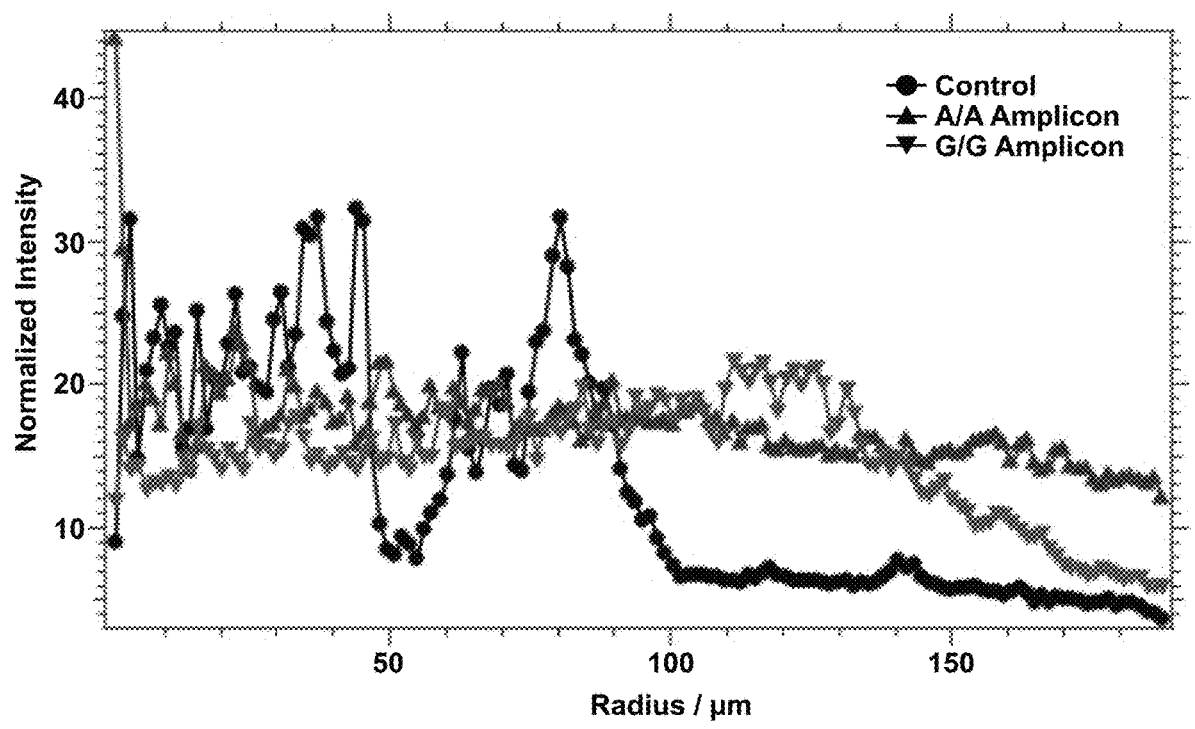
FIG. 7G

METHOD AND SYSTEM FOR BIOLOGICAL INFORMATION PATTERN STORAGE AND READOUT

CROSS-REFERENCE TO RELATED APPLICATIONS

This application claims the benefit of U.S. Provisional Application No. 62/680,908, filed on Jun. 5, 2018, which is incorporated by reference to the extent not inconsistent herein.

REFERENCE TO A SEQUENCE LISTING

A sequence listing containing SEQ ID NOs: 1-5 is provided herewith in a computer-readable .txt file and is specifically incorporated by reference.

FIELD OF THE INVENTION

Provided herein are methods and systems for acquiring, storing, detecting, monitoring and reading Biological Information Pattern (BIP) when a biological species is encoding digital information, within a liquid droplet exhibiting a pattern feature when drying onto a substrate, that can be perturbed by at least one physico-chemical interactions that can modulate specifically the wetting line pattern of said biological species into an information data status that may be detected by an imaging system. Included are methods and systems for detecting and processing biological perturbations that may occur in biological, chemical, or physical exposure of biological species, and preferably nucleic acids (e.g. DNA, RNA) or proteins, in particular when said biological is encoding some digital information (e.g. picture, written text). These BIPs may comprise an array of dried patterns of small volume of liquid droplets containing specific sequences of DNA base pairs coding digital information, said droplets that can be adsorbed onto a substrate preferably coated with molecular materials that can interact specifically with the DNA sequences through specific recognition mechanisms, such as a hybridization reaction that can be detected by imaging a change in the drying pattern.

BACKGROUND

There is growing interest in using synthetic Nucleic Acid (DNA, RNA) for information storage as the need for data storage capacity is expected to keep increasing, at an even higher rate, in the next decades. The ability of biological material, including a sequence of DNA to store a tremendous amount of information for all essential life functions (replication, growth, physiological activity, etc.) using only 4 four nitrogen bases, namely A (adenine), C (cytosine), G (guanine), and T (thymine) grouped in pairs (A-T and G-C) depending on the number of hydrogen bonds involved in the pair, is first reminiscent of how data is currently stored digitally (0 and 1 for logic semiconductor gates), but also opens up the possibility to increase the data density in a 4 state system. Since the pioneering work of N. Goldman et al (Nature 2013, 494, 77-80), there has been tremendous interest in a storage system using nucleic acid where information that can be stored in base 4, rather than a base 2 coding. This means, naively, a 4" rather than a 2" capacity. More recent works (Y. Erlich et al, Science 2017, 355, 950-954, or Bornholt et al, ASPLOS Proceedings, Apr. 2-6, 2016, Atlanta, Ga., USA) have tackled the reality that not all random sequences of nucleic acid bases are available due to, for example, the possibility of self-hybridization or the role of G-C isochores that could offer a subtler storage strategy. An alternative to using synthetized oligonucleotides assembled in vitro could rely on writing information into the genome of a living cell by the addition of nucleotides over time, for example by exploiting the CRIPR-Cas microbial system (S. Shipman et al., Nature, 2017). However, information stored in DNA is useless without efficient ways to readout the stored data at a reasonable speed. Although those reports of information storage in DNA are capable of capturing, storing or even propagating information over time, provided herein is a novel system to acquire and read data information stored in nucleic acids, or other similar biomolecules, compatible with the extraordinary high density information encoding and storage that DNA may offer over more conventional solid states or optical techniques.

SUMMARY

Accordingly, the embodiments presented herein can provide methods and systems for recording, processing, archiving and delivering digital information encoded into a molecular medium (e.g. DNA, RNA, amino acids) that can be interrogated by imaging its phase change motifs through an interaction between a liquid state and a solid substrate, that can serve as a mechanism of formation of a Biological Information Pattern (BIP) whose array can provide an efficient write-and-read data storage system.

Provided are methods of storing and retrieving digital information in a biological system, including by: translating digital information to a biomolecular medium. Biomolecular medium is used broadly herein to refer to a biological construct where digital information can be stored in the form of the basic biological constituents of a biological sequence. For a polynucleotide, the biological constituents are the fundamental bases A, T, G, C (with U replacing T for RNA sequences); for polypeptides, the biological constituents are the amino acids. For any of the biomolecular mediums described herein, the sequence may correspond to a nucleic acid molecule. A microarray comprising a substrate receiving surface and a plurality of unique substrate-bound sequences in a selected pattern is provided. The pattern of the unique surface-bound sequences are designed and configured to provide an end read-out, referred herein as a "biological information pattern" that is based on the encoded information in the biomolecular medium. This may be achieved by, for example, depositing a liquid droplet, or an array of liquid droplets, to the substrate receiving surface, wherein the droplet comprises the biomolecular medium and drying the liquid on the substrate receiving surface. Such drying can form a progressive recession of a wetting line and a corresponding dried residue pattern, wherein the recession of the wetting line and corresponding dried residue pattern is influenced by an interaction or a lack of interaction between the biomolecular medium and the plurality of unique substrate-bound sequences. This change in the wetting line (shape, position, line length, shape, curvature, surface area) as the fluid dries, and the resultant dried residue pattern, is generally referred herein as a biological information pattern (BIP). The dried residue pattern may be imaged with an imager. The image of the dried residue pattern may be processed with a processer to thereby decode digital information stored in the biomolecular medium. For example, the processer may implement one or more pattern recognition algorithms based on optical data to detect the BIP, including edge detection, to efficiently image the pattern without any labels or complex imaging components.

Rather, the imaging may simply be with a camera in a hand-held device, such as a smart-phone, or a tablet.

Accordingly, any of the methods provided herein are label-free in that no tag or other image-enhancing material need be used in order to successfully image a pattern to achieve a useful readout. The method may have an imaging step that is a sensor in a hand-held or mobile device, including a CMOS-based camera sensor.

The biomolecular medium may comprise three regions: a bead-binding sequence region; a substrate-binding sequence region; and a digital information region positioned between the bead-binding and substrate-binding regions.

The biomolecular medium may comprise a nucleic acid sequence, an amino acid sequence, or a combination thereof and the substrate-bound sequences correspondingly comprise a nucleic acid sequence, an amino acid sequence, or a combination thereof. The biomolecular medium may comprise a plurality of short-stranded ssDNA, optionally of a length of between 20 and 50 nucleotides. The biomolecular medium may be suspended in a liquid medium, may be introduced to a liquid medium, or may be on the substrate surface and a liquid medium applied thereto.

Any of the liquid droplet(s) may further comprise beads suspended in the liquid, wherein the beads have a bead surface. A plurality of bead-bound sequences may be connected the bead surface, wherein the bead-bound sequences have a sequence-binding region configured to bind to a bead-binding sequence region of a target sequence. In this manner, a target sequence may bind specifically to a bead via the bead-bound sequences. The beads may be part of a polystyrene bead library.

In this manner, the biomolecular medium may bind to a bead at one end, and bind to the substrate at another, via the respective bead-bound and substrate-bound sequences. This can help facilitate controlled and optically detected wetting lines without a need for any special labels or indicators.

Also provided herein is a system that implements any one or more of the methods described herein. For example, provided are biological information pattern (BIP) systems for encoding and readout of digital information comprising: a microarray having: a substrate with a receiving surface and a plurality of unique substrate-bound sequences, each having a unique target sequence binding region. A liquid droplet or an array of liquid droplets are provided that can be deposited on the substrate receiving surface. The liquid droplet contains digital information stored in a biomolecular medium and optionally beads to help facilitate desired wetting lines and resultant dried residual patterns (e.g., BIP(s)). The biomolecular medium comprises: a plurality of target sequences, each target sequence having a target substrate-binding sequence region, a target bead-binding sequence region, and an information region positioned between the target substrate-binding sequence region and the target bead-binding sequence region. An imager may detect the BIP. The target sequence binding region of the substrate-bound sequences are configured to specifically bind to the target substrate binding sequence region of a target sequence. During use the liquid droplet and plurality of unique substrate-bound sequences form a BIP wetting line detected by the imager to provide a read-out of the digital information. As the liquid further dries, the wetting line may reduce to the boundary of a dried residual pattern.

The imager may comprise a camera to optically detect the BIP wetting line, including in a conventional hand-held device, such as a smart phone.

During use the liquid droplet and plurality of unique substrate-bound sequences form a wetting line detected by the camera to provide a read-out of the digital information.

A processor, either on-board or located at a remote distance, such as on a computing device including a hand-held device, may process the optically obtained data to obtain a BIP wetting line and correspondingly calculate a wetting line optical parameter. The wetting line optical parameter is one or more of: a geometric shape, a size, a location on the substrate receiving surface. The size may be a perimeter, a wetted area confined within a region defined by the perimeter, a contour characteristic or the like.

The read-out of digital information is a label-free readout of a specific dried residue pattern. Any of the BIP systems may further comprise: a plurality of beads in the liquid medium, wherein the beads have a bead surface and a plurality of bead-bound sequences connected the bead surface, wherein the bead-bound sequences have a target sequence-binding region configured to specifically bind to a bead-binding target sequence region of the target sequence.

Any of sequences described herein may be a polynucleotide sequence, such as comprising a nucleotide sequence.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

The above and other aspects, features and advantages of the present method and embodiments will be more apparent from the following more particular description thereof, presented in conjunction with the following figures, wherein:

FIGS. 7A-7G. Differences in drying pattern of a droplet containing PS beads modified with a complementary sequence to the 5' end of the EGFR amplicon on a surface modified with a complementary sequence to the 3' end when either no EGFR amplicon, the A/A allele, or the G/G allele is present.

Corresponding reference characters indicate corresponding components throughout the several views of the drawings.

DETAILED DESCRIPTION

Figure 1:
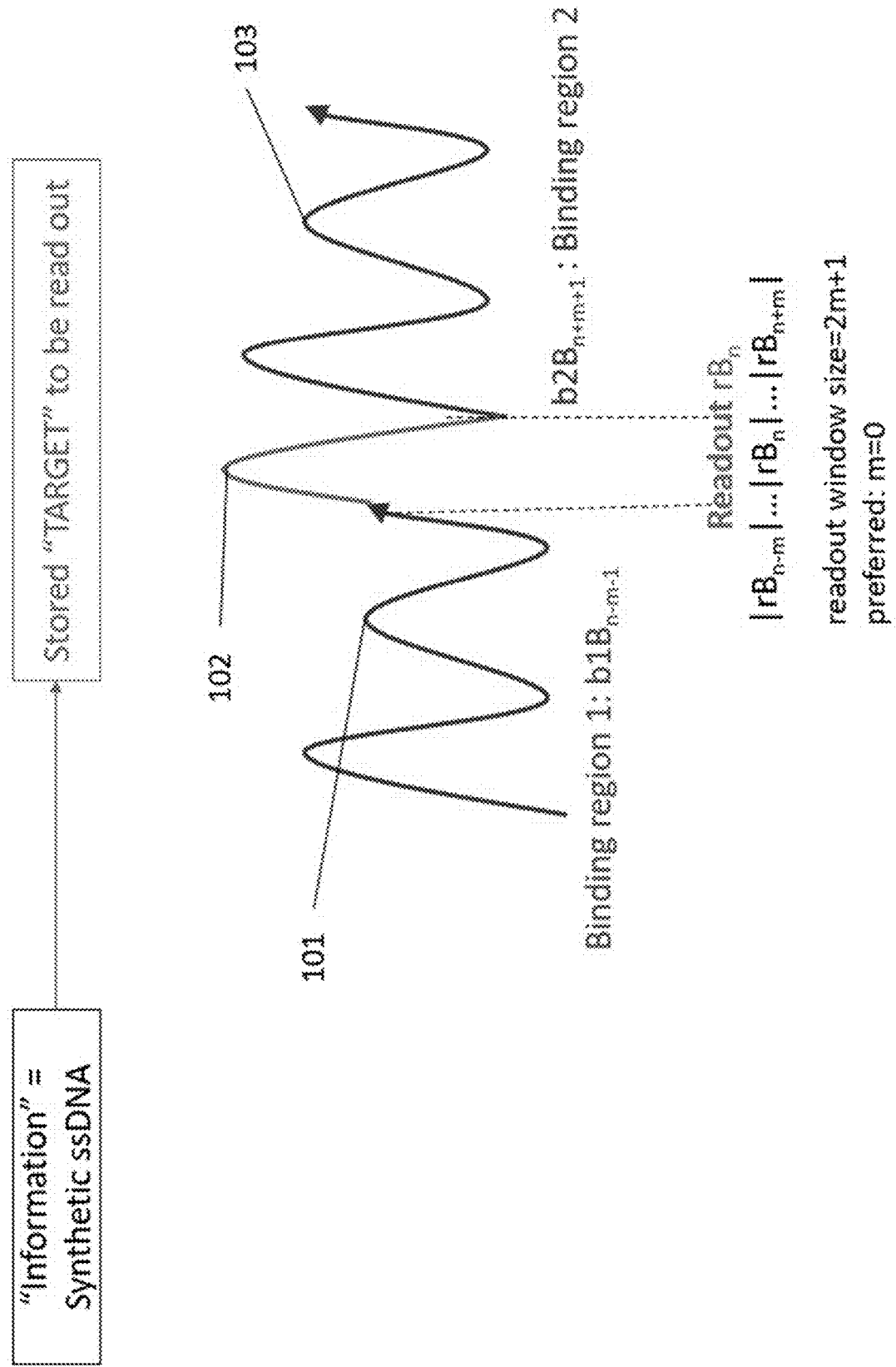
FIG. 1 is a schematic concept of the encoding digital information into a biomolecular medium ("translating").

The following description is not to be taken in a limiting sense, but is made merely for the purpose of describing the general principles of exemplary embodiments. The scope of the invention should be determined with reference to the claims. In general, the terms and phrases used herein have their art-recognized meaning, which can be found by reference to standard texts, journal references and contexts known to those skilled in the art. The following definitions are provided to clarify their specific use in the context of the invention.

If there are multitude of reports related to storage strategies, as well as methods to decrease the cost of synthesizing nucleic acid sequences, there is much less activity around the problems caused by the need of reliable, fast, and inexpensive methods to read out the information artificially stored in synthetic or microbial DNA. The reason for this trend may be that next generation sequencing (NGS) techniques are becoming more and more widespread for various applications and that, therefore, their currently high cost will drastically decrease in the future. This may not be entirely true as there are currently three major NGS methods available which all suffer from serious drawbacks for a widespread user-friendly everyday use to read out information stored in synthetic DNA sequences. A first standard approach is based on fluorescent readout of on-chip microarray libraries using bridge amplification through cluster formation and reversible sequence terminators (Lin et al. Recent Pat Biomed Eng. 2008, 60-67). A second standard approach uses an ion-sensitive field-effect transistor (IS-FET) to detect the amount of hydrogen ions released (change in local pH) during the DNA base pair dissociation. That method, however, requires lengthy amplification by emulsion polymerase chain reaction (PCR) and several other sample preparation steps (Rothberg et al, U.S. Pat. No. 7,948,015, 2011). A third approach uses the small current generated when each DNA base pair passes through nanometer-sized pores to identify the sequence. The device is fast (90 bases per nanopore per second) and compact but suffers from a 30% error rate and the data generated requires extensive data mining to be analyzed (Deamer et al, U.S. Pat. No. 6,015,714, 2010).

In order to overcome at least some of the limitations described above, provided herein is an array-based method to read out single base pairings in a short ($20<n<50$ base pairs) fragments of stored synthetic DNA in a highly-multiplexed fashion driving the drying pattern of micro- or nano-droplets containing the DNA-coded information to be read out. The method and system are rapid and inexpensive mainly, but not exclusively, because it uses bright field imaging and pattern recognition algorithms to perform the analysis. The method is compact and user friendly because current CMOS (Complementary Metal-Oxide Semiconductor) image sensors embedded in consumer smartphone cameras provide sufficient resolution and sensitivity to perform the analysis with very limited number of external optical elements. An important aspect is the way in which the array to decode the information is read out. The method and systems provided herein can use a truly label-free rapid read-out—as opposed to the traditional fluorescence-based readout for microarrays—based on the changes to the drying mechanism caused by a specific interaction with the surface and the ability to optically detect without a label, the wet/dry interface as the liquid dries.

Figure 2:
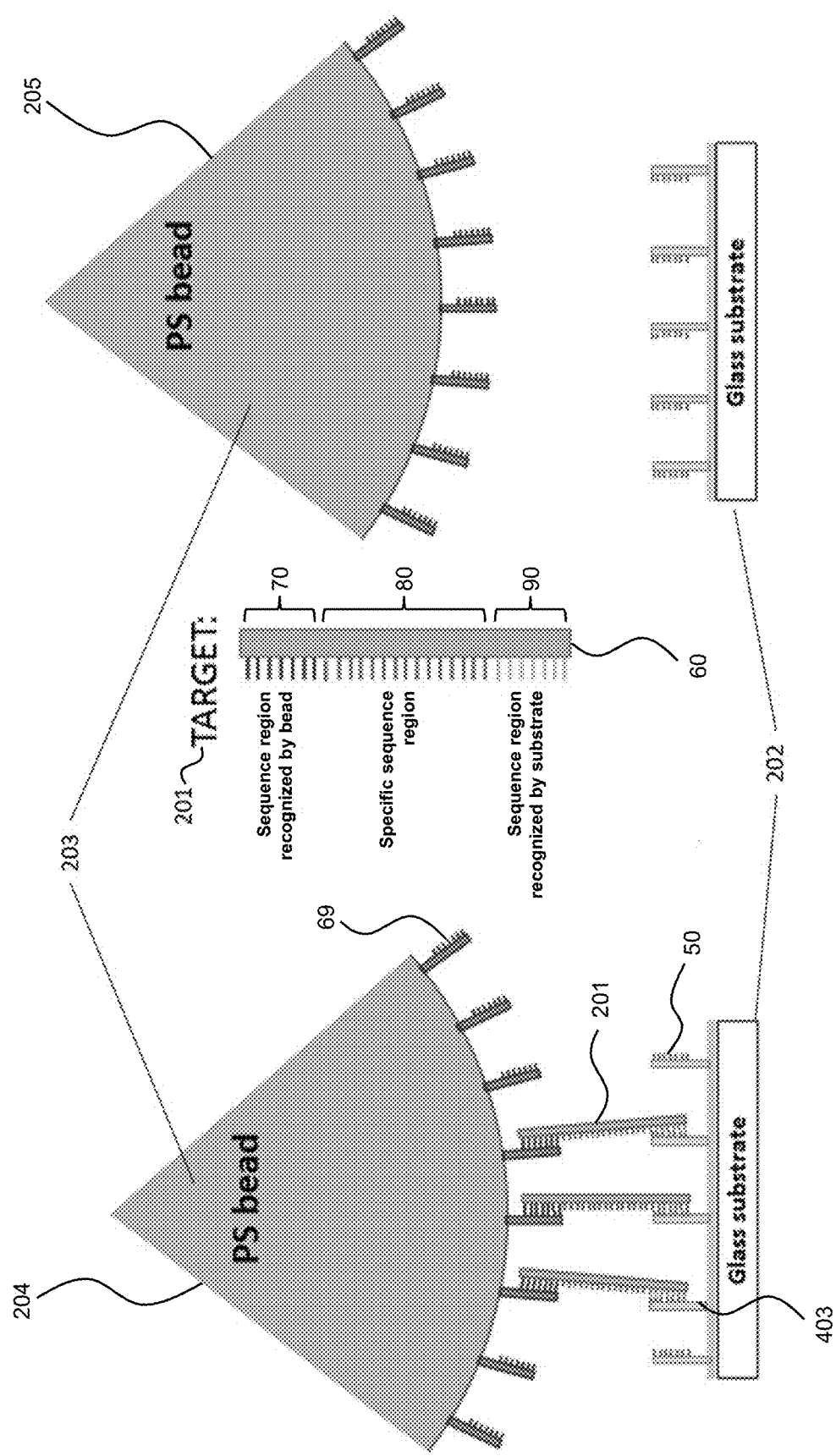
FIG. 2 illustrates an embodiment for the construction of the biological components used in the DNA capture system.
Figure 3:
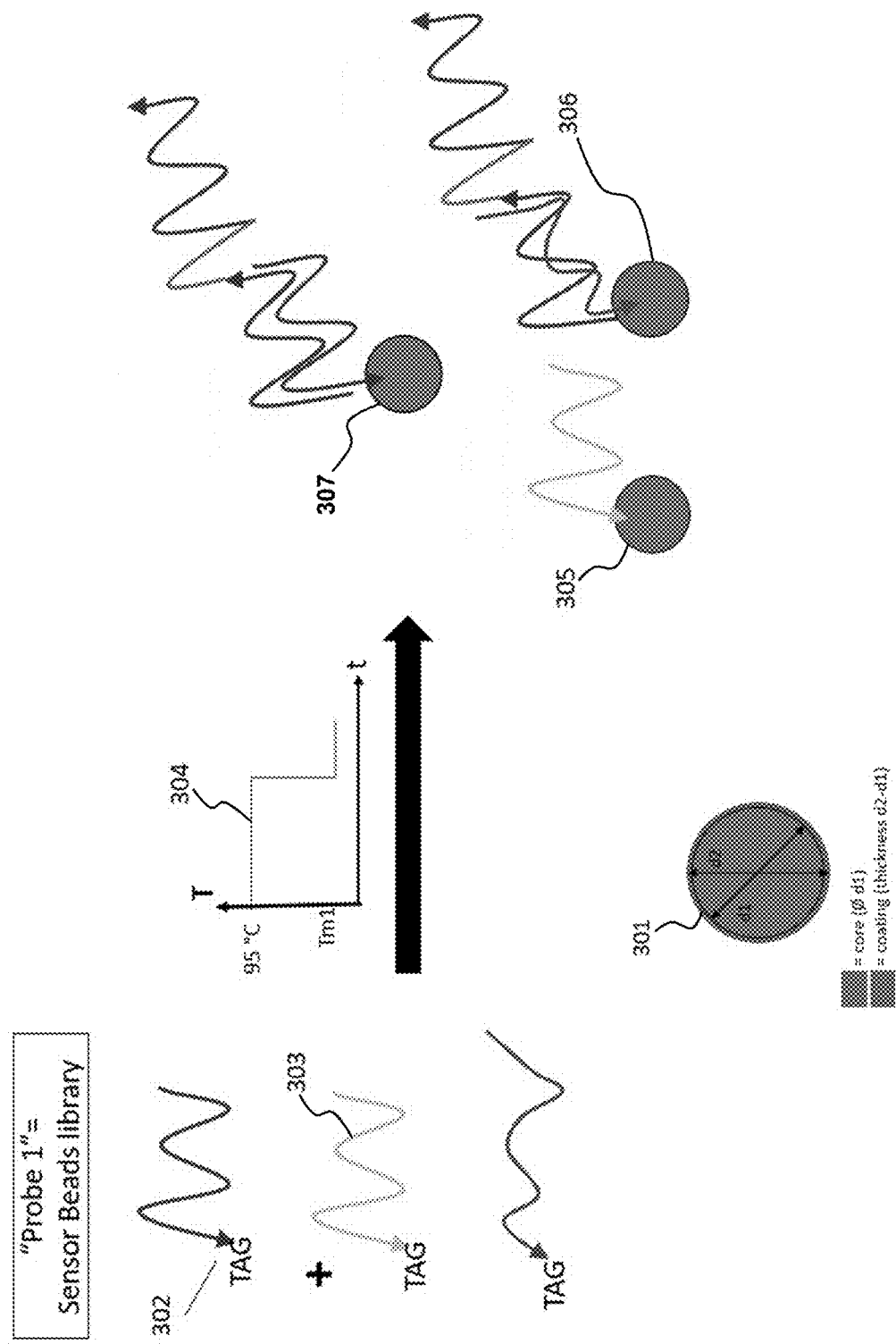
FIG. 3 is a system flow diagram in accordance with the method for acquiring, processing and delivering encoded biological information.
Figure 4:
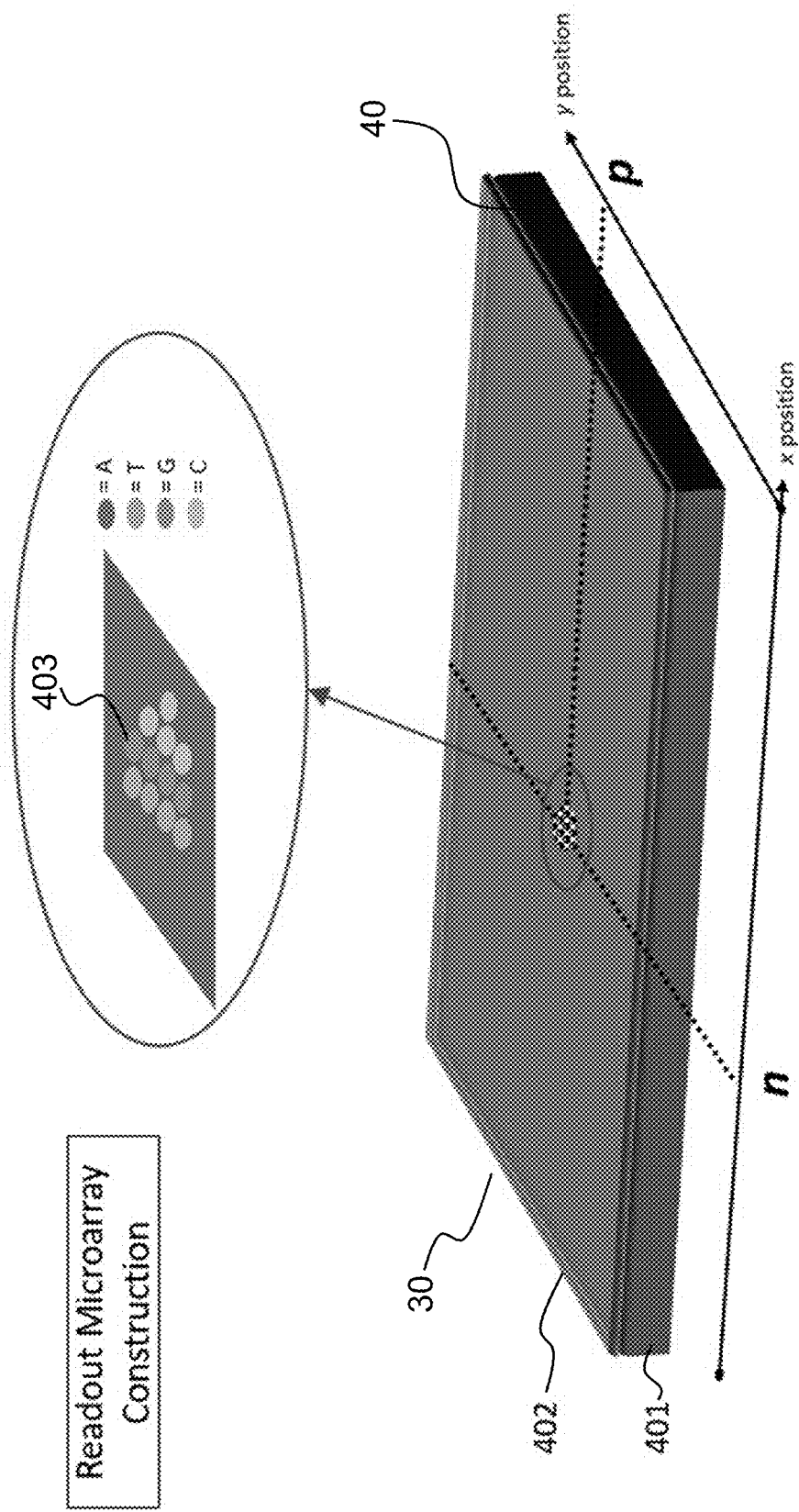
FIG. 4 illustrates an array configuration of the biological information pattern components onto a solid substrate.
Figure 5:
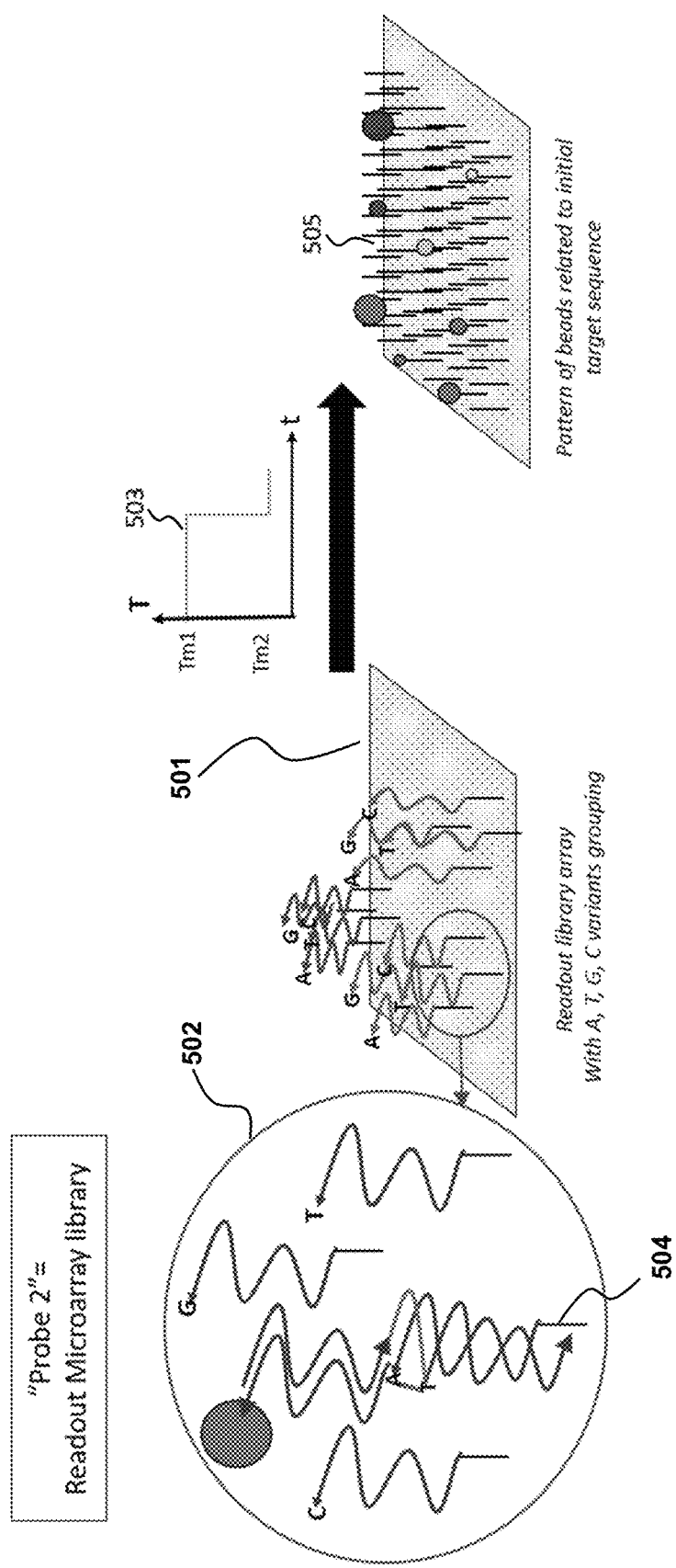
FIG. 5 illustrates a sequence of steps involved in the scale up of the BIP components and mechanism for building information storing.
Figure 6:
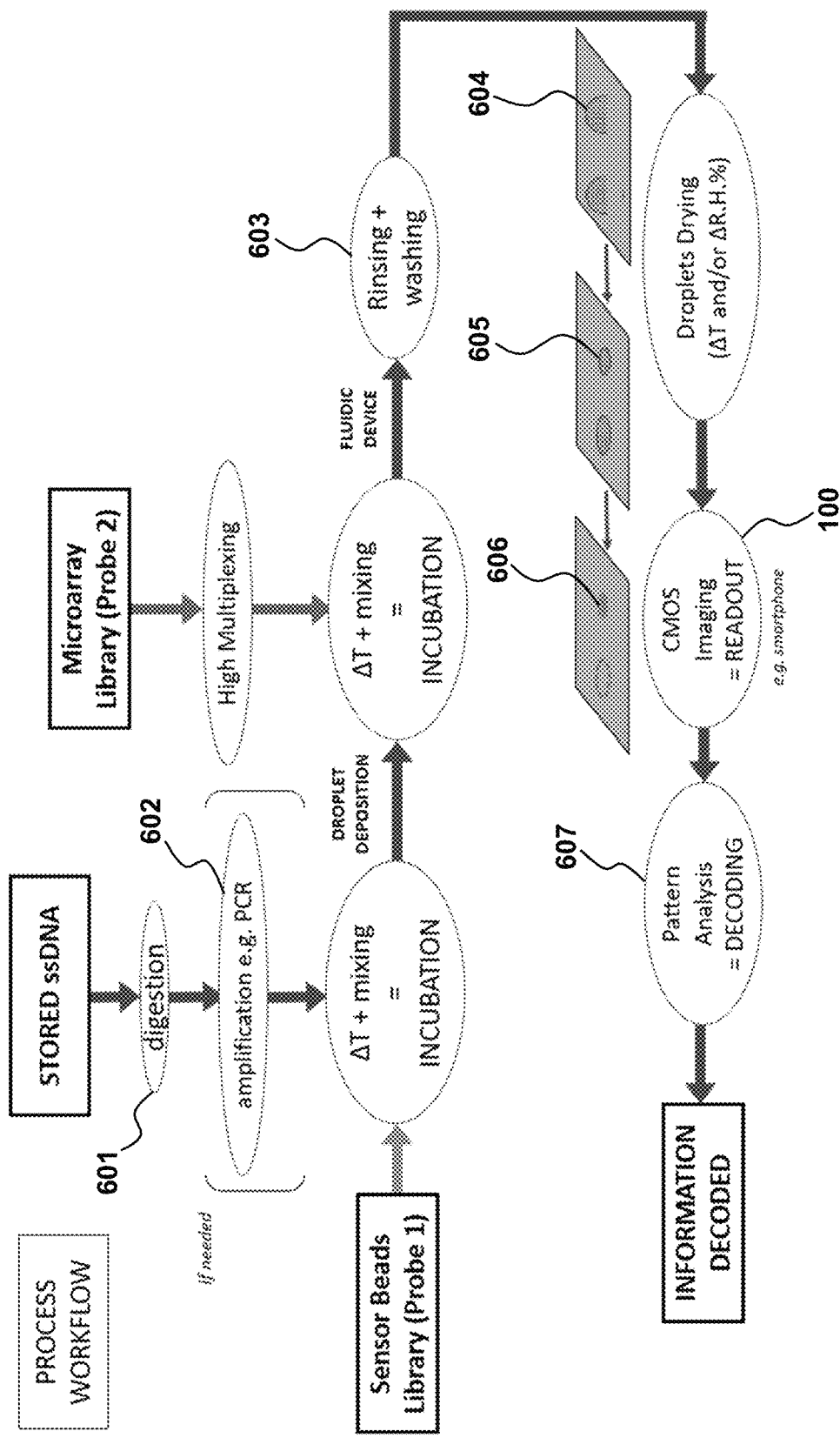
FIG. 6 depicts an overall workflow process for encoding of digital information and translation into high density molecular medium for processing and readout for reproducing some original digital information, ultimately.

Decoding a short storage single-stranded ssDNA fragment, named target information (biomolecular medium) in the rest of the document (FIG. 1), using only label-free observations of the drying mechanism of microdroplets (FIG. 2) is described. A library of short single-stranded nucleic acid (ssDNA) oligonucleotides coupled to coated polystyrene beads (FIG. 3) are incubated to hybridize a defined region of the storage DNA. The readout of the stored information is done using another library of oligonucleotides on a solid support (microarray with high multiplexing, FIGS. 4 and 5), also referred herein as a microarray substrate receiving surface with a plurality of unique substrate-bound sequences, each having a unique target sequence binding region. The microarray may be constructed in groups of A, T, G, and C to determine what the base at position n of the target information is for all p relevant positions of n (FIG. 4). A main point is how the microarray is analyzed (FIG. 2). Indeed, a sub-microdroplet (10 pL<volume<100 nL) is simply deposited onto the surface in each microarray area corresponding to position n and left to dry in a controlled temperature- and humidity-controlled chamber. The interaction strength (or its absence) determines a specific drying mechanism and, therefore, a particular pattern in the dried residue. The pattern is simply imaged with a camera sensor in bright field illumination conditions (e.g. a CMOS), and subsequently analyzed by software (processer) (FIG. 6). By analyzing the pattern obtained at each A, T, G, or C variant spot at each relevant position n on the array, the information stored in the target DNA fragment can be simply and quickly read out without cumbersome and expensive apparatus. This addresses the need for portable readers to follow the current fast development and maturation of storing information in DNA rather than silicon-based semiconductors. See, e.g., Example 1 titled "Influence of a single nucleotide polymorphism (SNP) and DNA hybridization on the drying patterns of microdroplets."

The target storage DNA information may be divided in 3 parts (FIG. 1) from the 3' to the 5' end. A first region (101) is termed the bead-binding sequence region, or binding region 1, since it will hybridize with the bead-coupled complementary strand from the library with highest affinity. The central region is defined as the readout region (digital information region) (102) and is comprised of 2m+1 bases that will be read out at position n on the microarray. Preferably, m=0 to allow for single base readout and reduce the amount of multiplexing on the array as well as the complexity of the analysis software. In cases where the target information fragment presents only weak interactions with the libraries, the readout region can be extended to m=1 or 2. Finally, the last region on the target information DNA can be called the surface-binding region (substrate-binding sequence region), or binding region 2 (103), and hybridizes with the complementary sequence on the microarray library, which extends into the readout region. The target storage DNA may be divided into regions as specified above in a single-stranded (ss) oligonucleotide sequence platform with a length of nt nucleotides. nt is the sum of nucleotides in all 3 regions, i.e. nt(total)=nt(b1)+nt(rB)+nt(b2) across regions b1 (bead-binding), rB (readout), and b2 (surface-binding). For the optimal and fastest results of the disclosed method, the total length is limited as defined: 0<nt(total)<60 to avoid negative effects arising from self-dimerization in longer fragments.

FIG. 2 illustrates a main concept of a readout method for a specific DNA target (201, and FIG. 1 for details) based on the pattern of the final residue of each droplet. Two extreme situations can be distinguished. In both cases, the coated polystyrene (PS) beads that constitute the sensor beads library (202 and FIG. 3) are mixed with the target DNA and deposited onto a glass substrate chemically modified with a library of oligonucleotides or sensor array (203 and FIG. 4). In the presence of the complementary oligonucleotide on the sensor array, a strong interaction force between the bead and the surface mediated by the storage DNA to decode will occur and cause the beads to uniformly deposit on the surface as the wetting line recedes (204). In the presence of a non-complementary sensor array oligonucleotide, the beads will follow the wetting line and slide over the surface without any significant interaction (205). These different situations result in different pattern in the dried reside of each droplet on the surface.

The sensor beads library (FIG. 3), or probe 1, may be constructed as follows. The first element comprises a polystyrene core bead (301) coated with a layer showing affinity for a specific chemical tag (302) present at the 5' end of a single-stranded oligonucleotide library complementary to the bead-binding region 1 (303). The tag at the 5' end of the library oligonucleotide is—preferably, but not limited to biotin, a thiol, and amino, or a carboxyl functional group. In this case, the bead is coated with streptavidin, a thiol function, a carboxyl rich covalent or polymeric layer, and an amine-rich covalent or polymeric layer, respectively. The ssDNA oligonucleotide library is approximately made of $4^{(nt(b1))}$ sequences to take into account all combinations possible in binding region 1. Each bead-coupled library oligonucleotide is characterized by a unique melting or hybridization temperature Tm1. If needed to avoid steric hindrance during nucleic acid hybridization, a chemical spacer arm constituted of several A nucleotides or a carbon chain can be added between the bead and the oligonucleotide during synthesis. To promote selective and stable hybridization of the library and the target ssDNA information, a temperature ramp (304) is applied during incubation first at 95° C. (to dissociate all library components and reduce negative effect from intra-library hybridization and cross-reactivity), then quickly ramped down to the Tm1 melting temperature of the calculated complementary region to the target information ssDNA. After incubation, the library consists of unmatched, non-hybridized fragments or "unmatched library strands" (305), weakly matched fragments or "weakly matched library elements" (306), and, most importantly, a single type of matched library elements (i.e. complementary) fragment (307).

The highly multiplexed readout microarray (FIG. 4) comprises, preferably, a solid support (401) such as borosilicate glass, silicon/silicon oxide, or, for example, polymeric plastic such as polycarbonate (PC) or cyclic olefin copolymer (COC) with a polymer or monolayer coating (402) to promote the chemical attachment of modified oligonucleotides to sense the stored DNA fragments. The position n along the length of the array corresponds to the base read at position n in the expected sequence of the stored DNA to decode. The position p in the width of the array corresponds to a particular combination of the n first bases of the DNA to decode. The (n, p) coordinate on the array is subdivided in k replicates (preferably k=4) of the 4 possibilities for the nth base of the stored DNA, namely A, T, G, or C (403). Each analyte region on the array is made using standard spotting techniques, such as non-contact piezoelectric dispensing (Malcolm et al, US Patent Pub. No. 2009/0227476, 2009).

A second part of the detection scheme is the highly-multiplexed microarray (501) with a second oligonucleotide library. See, e.g., FIG. 5. The library comprises surface-coupled ssDNA complementary (matched with) to binding region 2 at a given position n on the array. At each position n, a given sub-item in the library is further multiplexed into 4 surface-coupled ssDNA oligonucleotides terminated with A, T, G, or C, respectively (502). The complementary surface oligonucleotide specifically binds region 2 of the target information DNA with a precise melting temperature Tm2. Therefore, the surface is first maintained at Tm1 to preserve the hybridization to the target information DNA in region 1 (where the bead is attached to), then ramped to Tm2 to promote the specific binding to the matched sequence on the surface (503). To ensure stable chemical binding of the region 2 library oligonucleotides on the surface, the 3' end of each fragment is affinity tagged (504) with for instance, biotin, a thiol, an amino or carboxyl functional group. When needed, a spacer arm is added to prevent steric hindrance during nucleic acid hybridization. The surface is coated with the corresponding chemical derivatization, i.e. streptavidin, a thiol, a carboxyl, or an amino function, respectively, depending on the chosen affinity tag. The result of the second selection by the microarray library, upon drying of the multiplexed sub-microdroplets containing the storage DNA to decode, is a series of dried residue with distinctive patterns. The patterns obtained will vary when beads are present at each position n (corresponding to the base Bn in the target information DNA) on the particular A, T, G, or C variant on the array (505). To facilitate and speed-up the readout, beads of different sizes, coloration, composition or fluorescent properties can be used for different base positions in the target information. In the preferred embodiment, polystyrene beads of diameters 0.5-5 μm are used. To better control the drying process of the beads on the microarray surface, the properties of the droplet fluid can be tuned by changing the solvent and adjusting the initial wetting angle through hydrophobic/hydrophilic interactions. The drying process can also be slowed down by adding glycerol or polyethylene glycol to reduce the evaporation rate. Droplets in deionized filter water may be used. The array (and the sensing beads library) does not necessarily contain all the oligonucleotides to sequence the entire stored DNA fragment as this would make the array far too complex and expensive. Instead, the sensor array and the beads library are encoded in a way that matches how the information is coded onto the stored DNA fragment that is read out. This opens another area of innovation in terms of secure communication based on information stored in the DNA target to decode. The information encoded in the DNA is read by the proper array and beads library that match the algorithm used to store the information in the specific sequence of oligonucleotides of the target. If the wrong array is used, the decoding is false.

FIG. 6 describes an overall process workflow. After the digital information is encoded into biomolecular medium using various coding algorithms (see, e.g., G. M. Church, et al., Science 337, 1628, (2012); Y. Erlich et al., Science, 355, 950-954, 2017), the stored DNA (target information) can be digested (601) using restriction enzymes, if necessary, to create sub-fragments between 20 and 60 bases, where the method is most efficient. In rare cases where more material is needed to readout the information contained in the DNA, amplification via Polymerase Chain Reaction (PCR) can be implemented (602). Preferably, a TaqMan amplification will be most suited to reduce the amount of error in base replication. When the analysis time is of concern, an isothermal amplification (e.g. Loop-Mediated Isothermal Amplification (LAMP)) can be added instead. The sensor beads and microarray library generation as well as the different incubation steps have been previously described. A disposable plastic fluidic device pre-loaded with all necessary reagents is used to automate and streamline the washing and rinsing steps (603) to remove non-specifically bound DNA material from the microarray surface. The final steps leading to the information readout comprises: (i) depositing several droplets (10 µL-100 nL) onto the array derivatized with the oligonucleotide library for binding region 2 (604) in a temperature and humidity-controlled environment using for instance Peltier elements or resistive elements and water-glycerol solutions (Forney et al, HortTechnology 1992, 2, 52-54); (ii) allowing the droplets to dry, preferably without forced convection, by progressive recession of the wetting line (605). The presence of a specific molecular interaction between the coated beads and the coated surface significantly modifies (606) the drying mechanism at the wetting line (Hurth et al, Chemical Engineering Science 2015, 137, 398-403); (iii) using analysis of the dried residue pattern (607) upon imaging with a high resolution CMOS camera sensor to obtain information on the content of the initial droplet (Kim et al, Analytical Methods 2012, 4, 50-57). For example, the algorithm relies on identification using a combination of color distribution, local binary pattern, Gabor wavelet, and size and a training data set.

Provided herein is a method for making a biological information pattern array for encoding, processing and storing representative digital data information that can be read out through the inspection of said patterns by an imaging technique for retrieving said digital information, the method comprising:

1) translating digital information into biomolecular medium, preferably a nucleic acid molecule, using an encoder algorithm;

2) Designing a biological information pattern by depositing onto a sensor surface a liquid droplet, or array thereof, containing said biomolecular medium and letting said droplet to dry by progressive recession of the wetting line forming a specific dried residue pattern;

3) Reading out the content of information using a label-free visualization of the dried residue pattern by imaging with a high resolution CMOS camera sensor; and 4) Processing the image information for decoding the digital data stored in the biological medium.

Referring to the figures, a biological information pattern (BIP) system 501 for readout of digital information stored in a biological medium comprising: a microarray 30 having: a substrate 401 with a receiving surface 40 and optionally a coating layer 402 supported by the receiving surface 40; a plurality of unique substrate-bound sequences 403, each having a unique target sequence binding region 50; a liquid droplet or an array of liquid droplets 604 deposited on said substrate receiving surface, wherein said liquid droplet comprises beads 203 with sequences 69 attached thereto and contains digital information stored in a biomolecular medium 60 and said biomolecular medium comprises: a plurality of target sequences 201, each target sequence having a target substrate-binding sequence region 90, a target bead-binding sequence region 70, and an information region 80 positioned between the target substrate-binding sequence region and the target bead-binding sequence region; an imager 100 to detect the BIP; wherein the target sequence binding region of the substrate-bound sequences are configured to specifically bind to the target substrate binding sequence region of a target sequence; and wherein during use said liquid droplet and plurality of unique substrate-bound sequences form a BIP wetting line 605 606 detected by said imager to provide a read-out of the digital information. A processer 607 may be used to calculate a wetting line optical parameter based on the wetting line, including a wetting line that is dependent on drying time.

Example 1

Influence of a Single Nucleotide Polymorphism (SNP) and DNA Hybridization on the Drying Patterns of Microdroplets A specific molecular recognition between coated polystyrene (PS) beads dispersed in solution and a solid surface can drastically change the process by which microdroplets of fluids dry. This observation simply relies on the analysis of the final dried residue on the surface, therefore involving minimal intervention by trained individuals and a minimum investment in sophisticated readout equipment. For instance, a smartphone CCD camera suffices to provide the data required for the analysis. These recent results naturally open the possibility of developing an inexpensive point-of-care diagnostics method for diseases with a known genome recognition sequence—or a monoclonal antibody signature—using biomedical approaches at the molecular or sub-nanometric level. The present results validate the feasibility and sensitivity of the exposed method for the characterization of a known SNP (single Nucleotide Polymorphism) in the Epidermal Growth Factor Receptor (EGFR) gene (dbSNP ID: rs1050171) identified as an early biomarker for several cancers.

For many decades, research on how the contents of a droplet can modify the drying mechanism has been going on with most studies focusing on transport processes such as the pinning of a wetting line [1,2] with some studies tackling how changes in the surface properties can affect the process as well [3-8]. Understanding how a specific molecule-receptor interaction at the solid surface affects the drying mechanism and the pattern of the final residue has promising bio-medical applications. For instance, it could be employed for the detection of biomarkers in biological fluids (e.g. effusions or blood) using an immunoassay where an antibody immobilized on the surface binds with high affinity to a specific biomarker in solution. Such a molecular recognition event is different from nonspecific van-der-Waals and electrostatic interactions studied so far [5,8]. A specific biomolecular interaction between the surface and solute beads modifies the expected drying mechanism [9]. In general, nano- or micro-sized beads are an efficient approach to disrupt drying mechanisms because solute particles have a strong effect on the droplet drying process [1] and the tunable properties of the particles make them amenable to biological applications [10]. The instant methods, coupled to complex pattern-recognition algorithms [11], provides direct diagnosis of disease conditions for remote point-of-care applications. A first step, however, is to investigate how DNA hybridization on the surface affects the drying sequence since the specificity and thermodynamic stability of DNA base pairing creates more suitable experimental conditions for a stronger response to validate the proposed platform technology.

The biotin-streptavidin (SAv) system was initially selected for its known strong non-covalent protein-cofactor interaction, with a dissociation constant, $K_D = 4 \times 10^{-14}$ M [12], or a measured stretching bond force of about 160 pN per biotin-streptavidin bond [13]. The results we obtained are applicable to the study of a biomarker in solution, or immobilized onto the surface, by tagging the biomarker or its receptor with either biotin or streptavidin. To initially investigate how a model system such biotin-streptavidin influences the droplet drying process, we considered aqueous dispersions of biotin- or SAv-coated fluorescent polystyrene (PS) particles. Encouragingly, we witnessed how beads coated with a molecule (biotin) with high affinity for a ligand coated on the surface (streptavidin) dispersed in solution can modify the drying process of a 0.1-0.2 μL droplet and the final dried residue pattern [9]. Maximum sensitivity is achieved using biotin-coated polystyrene beads (diam. 0.5 μm) and streptavidin-coated glass slides. A control experiment consisted of drying similar streptavidin-coated beads in the same conditions. In both cases, the particles first gather into forming a large peripheral ring. This indicates a strong contribution from radial flow and that the drying process is driven by evaporation at the wetting line. As the water evaporates, particles experience Brownian motion and the ring diameter stays constant. The two systems behave differently in the final stage: while most streptavidin-coated beads deposit in the central region of the droplet residue with fewer particles in the peripheral ring, the biotin-coated particles are much more uniform. The same observation can be drawn from comparing the radial particle distribution profile in a 90-degree quadrant area centered at the geometrical center of the droplet and with the radius of the external peripheral ring. About 30 s after the deposition, the distribution profiles show beads uniformly distributed around the center for both biotin- and streptavidin-coated solutions. However, the biotin-coated beads distribution will retain a uniform angular distribution whereas the streptavidin-coated beads are concentrated within the first 50 μm of radius values. These results show the different outcome due to the existence of biomolecular force that resists the wetting force of the receding wetting line.

To understand how biomolecular interactions can prevent beads, which are attached to a solid-liquid interface, from sliding along with a moving fluid, we considered the balance of the forces acting on a bead and formulated a mechanistic analytical model for one bead near the wetting line of the evaporating droplet. For a dispersion of biotin-coated beads drying on a surface coated with streptavidin, there is a biological bonding force that resists the receding of a wetting line, leaving the original drop area covered with beads that have been left behind the receding wetting line. For a dispersion of streptavidin-coated beads instead, the beads will recede with the wetting line and accumulate in larger number at the center of the original drop area. In our calculations, the biological force is 3 orders of magnitude larger than the drag force.

The sensing method is based on selective oligonucleotide hybridization. The polystyrene beads and glass surface are selectively chemically modified with an oligonucleotide sequence complementary to different regions of the target DNA sequence. The target DNA sequence should be kept short (20-60 base pairs) to avoid self-dimerization within longer fragments that will prevent proper hybridization with the probes on the beads and on the surface.

To test our assay approach (FIG. 2), we selected the model system of a SNP in the EGFR gene (dbSNP ID: rs1050171) using several synthetic oligonucleotide sequences coupled to the sensing moieties at two different levels:

(1) Streptavidin-coated glass surfaces are modified with a short 24-bases nucleotide complementary to the 3' end of rs1050171. This oligonucleotide is labeled with biotin at the 3' end to facilitate its attachment to the surface.

(2) Streptavidin-coated PS beads (diameter: 0.4-0.6 μm, SVFP-0552-5, Spherotech, Inc.) are conversely modified using 36-bases oligonucleotides of two types complementary to the 5' end of rs1050171. One oligonucleotide is complementary to one allele (T at position 26) whereas the other one contains a mismatched base (G at position 26). Once again, these oligonucleotides are labeled with a biotin at the 5' end for coupling to the streptavidin-coated beads. Table 1 summarizes the oligonucleotide sequences and their relation with rs1050171.

When the target EGFR sequence is present below the detection limit (or absent), the sensor beads are expected to "slide" on the sensor substrate. Above the detection limit, the target EGFR DNA amplicon serves as a bridge between the sensor substrate and the sensor bead creating a stable specific hybridization interaction between the beads and the surface leading the beads to "stick" and perturb the receding wetting line.

Calculation of Hybridization Parameters

Theoretical values of melting temperature, $T_m$, and the free energy of hybridization with the context sequence, $\Delta G_{int}$, were computed using NetPrimer (PREMIER Biosoft, Palo Alto, Calif.). Table 1 summarizes the oligonucleotide sequences used in relation to the target context sequence as well as $T_m$ and $\Delta G_{int}$ values.

The oligonucleotides selected to coat the beads and the surfaces are checked against hairpin formation and excessive GC content. The possible interaction between oligonucleotides (cross-dimers) was estimated using NetPrimer. No cross-dimers with a free energy of hybridization $\Delta G_{int}$ lower than −8 kcal/mole were found; this guarantees only specific hybridization events in our experimental design.

In order to reduce the $T_m$ values, the beads and surfaces modified with the biotinylated oligonucleotides are used in a final buffer (e.g. 10 mM Tris, 1 mM EDTA, pH=8.0) at high salt concentration (1-5 M NaCl). High monovalent salts contribute to reducing the hybridization temperature and reduce the annealing times [14].

Beads and Surface Modification with Sensing Oligonucleotides

The glass beads are coated with 5'-biotinylated oligonucleotide using the following procedure [15]. 0.5 mL of the stock beads (Spherotech SVFP-0552-5) at 0.1% w/v in 0.1 M PBS, pH=7.4 were vortexed and centrifuged for 2 min at 14,000 rpm (16,000 g), then re-suspended in 0.2 mL 0.1 M Tris, pH=7.4 (Sigma Cat. T1944) and centrifuged for 4 min at 14,000 rpm. After resuspension in 10 mM Tris, 1 mM EDTA, pH=8 (Fluka Cat. 93283), 20 μL oligo stock was added at a final concentration of 10 μM. The solution was incubated for 1 h at RT (≈22° C.) on a spinning wheel, and then centrifuged for 4 min at 14,800 rpm. The beads were washed with 0.2 mL deionized water, centrifuged for 1 min at 14,800 rpm, and re-suspended in 0.2 mL 10 mM Tris, 1 mM EDTA, 0.5 M NaCl, pH=8 (Teknova Cat. T0231) for further use.

Similarly, the streptavidin-coated (SAv) glass slides are derivatized with 3'-biotinylated oligonucleotides. 30 µL droplets of stock (100 µM) 3'-biotin oligonucleotide solution are deposited on the surface using a micropipette for 30-60 s. The spots modified with the oligonucleotides are then rinsed with the same volume of deionized water by pipetting the volume back and forth on the surface with the pipette 3-5 times to ensure proper wetting of the surface and removal of non-specifically bound oligonucleotide.

Experimental Procedure

The details of droplets to be deposited on the 3' biotinylated oligonucleotide glass slide surface are given in Table 2. To evaluate the specificity of the method, Type 1 bead-coupled 5' biotinylated oligonucleotides (T variant) as well as Type 2 bead-coupled 5' biotinylated oligonucleotides (G mismatch) are deposited on the streptavidin surface. For Type 2 beads, the interaction between the modified beads and surface is expected to be weaker and the beads should mostly slide off the surface even in the presence of high EGFR A/A amplicon concentrations.

The beads are deposited on the surface using the following method. A 50 µL volume of oligonucleotide-bound beads was first heated to 72° C. on a PCR cycler (Eppendorf Mastercycler® nexus) while shaking the sample tray at 650 rpm. The EGFR PCR amplicons ([A/A] and [G/G] alleles) were denatured at 95° C. for 90 s and placed on ice. The solutions listed in Table 3 are then incubated at 72° C. while mixing at 650 rpm for 30 min and diluted 1:2000 with Teknova T0231 buffer. 0.1 µL droplets were then deposited on the SAv surface with 3'-biotin-oligonucleotide using a Gilson P2 pipet on a heated glass slide and left to dry (T≈22° C., RH=30%) before imaging using fluorescence microscopy.

PCR Amplification of EGFR Target

To assess assay performance using DNA mixtures with known alleles, three control DNA samples from the Human Random Control DNA Panel 3 are used (Sigma-Aldrich). The genotype of control samples A02, A04 and A06 was evaluated using a quantitative PCR assay targeting SNP rs1050171 (TaqMan® Predesigned SNP Genotyping Assay Product Number C_2678675_20, Life Technologies, Foster City, Calif.). This assay uses two allele-specific probes containing distinct fluorescent dyes and a pair of PCR primers to amplify the target region and distinguish the two SNP alleles. Assays are performed on a LightCycler 480 Instrument II and allelic discrimination plots to identify control samples with homozygous A/A and G/G or heterozygous genotypes (A/G, 50% of each allele). Once control sample genotypes are known, the same assay was used to generate PCR amplicons using duplicates of the three control samples. 50-µL PCR reactions are performed using 45 µL Platinum PCR Supermix (Thermofisher), 1.25 µL of the assay, 1 µL of template DNA and 2.75 µL of molecular grade water. PCR is performed using the following conditions: 1 cycle at 94° C. for 2 min, 35 cycles of 94° C. for 30 s, 60° C. for 30 s and 72° C. for 45 s, 1 cycle at 72° C. for 1 min followed by a hold at 4° C. forever. PCR product is purified using magnetic bead purification (SPRIselect) using 1:1 volume ratio of bead buffer and PCR volume and eluted into 50 µL. The final DNA concentration is determined using the 260/280 nm method with a UV/Visible spectrophotometer and was typically around 2 ng/µL (0.1 µM).

Temperature Control and Imaging

A bare clean glass slide was placed on a copper wire mesh. The copper wire was then heated using a constant-current DC power supply until the temperature on the surface of a streptavidin-coated test slide placed on top of the bare glass slide, as measured by a Type K chromel-alumel thermocouple, was equal to the calculated $T_m$ value from Table 1. The glass heating apparatus comprises copper wire and a cover to maintain the temperature and humidity in close proximity of the surface. A linear relationship for the temperature with the supplied DC current was obtained to calibrate the heating system (data not shown) between 72 and 82° C. where a change of 3° C. occurred for a 0.1 A increase in the supplied current. Infrared thermal mapping of the glass surface using a portable FLIR E50 camera (FLIR Systems, Wilsonville, Oreg.) demonstrates a stable uniform temperature is obtained 70 s after flowing current through the copper wire.

The fluorescent polystyrene streptavidin-coated beads used either had a "yellow" (Spherotech, Inc. SVFP-0552-5) or "Nile Red" (SVFP-0556-5, Spherotech, Inc.) dye embedded in their core. They emit with a maximum at 500 and 560 nm, respectively, when excited at 488 nm. To visualize them, an inverted Nikon Ti-U microscope with a 10× objective and FITC and Cy3 filters sets was used.

First, the optimal coupling conditions between the biotinylated oligonucleotides, the beads and the surface are determined. The preferred bead concentration that shows a significant effect while allowing easy observation using fluorescence microscopy is determined and resulted in additional 1:2000 dilution before deposition. The surfaces and solutions are held at the calculated $T_m$ values for each oligonucleotide within 1° C. or less [15]. The chosen oligonucleotide concentration to derivatized the beads is determined given the measured streptavidin surface coverage provided by the manufacturer. A relatively high final concentration of PCR amplicon is selected to ensure the system works above its detection limit to illustrate, for the time being, the proof of concept of our proposed method. According to the model developed for the biotin-streptavidin model [9], the detection limit correlates with the minimum biological bonding force, or DNA hybridization force, that is generated to balance the drag force of the receding wetting line. The total number of particles on the surface of each experiments is determined using image thresholding and particle analysis in ImageJ (National Institutes of Health, Bethesda, Md.) limited to particles for sizes between 0 and 100 pixels$^2$ with a circularity from 0.0 to 1.0 (spherical). In each case, the number of particles on the surface is similar, which excludes any effect of the number of particles considered in the observed images. Typically, between 160 and 190 particles are deposited on the surface in the observed field of view of the drying 0.1-0.2 µL droplet.

Surface-Beads Interaction

Figure 7A:
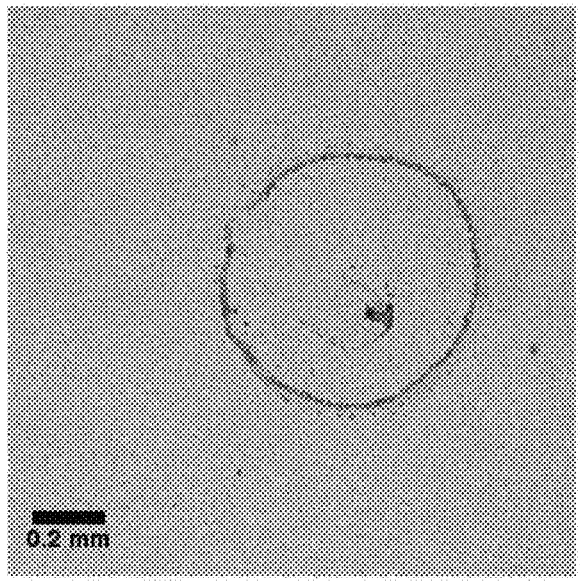
Figure 7B:
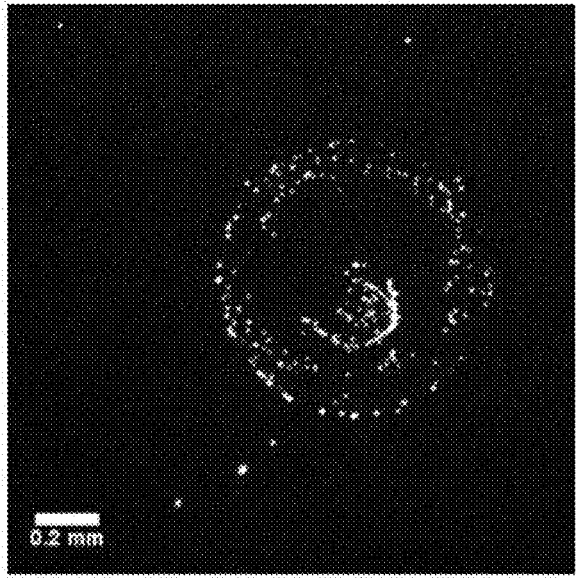
Figure 7C:
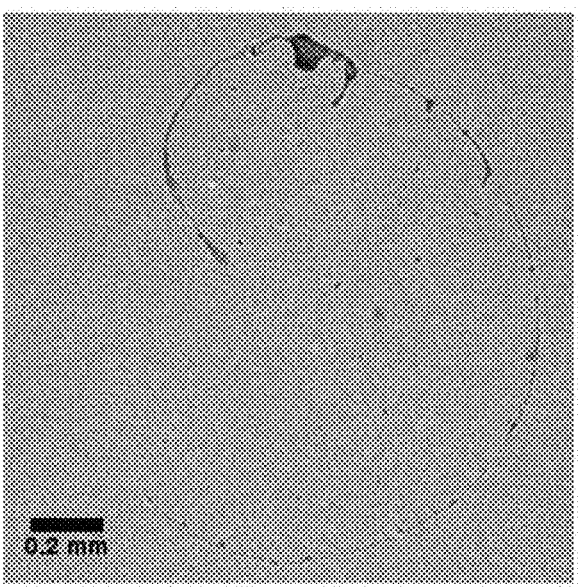
Figure 7D:
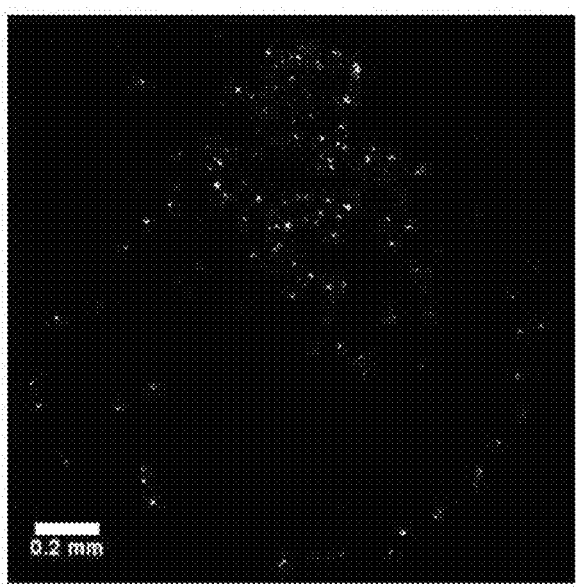
Figure 8A:
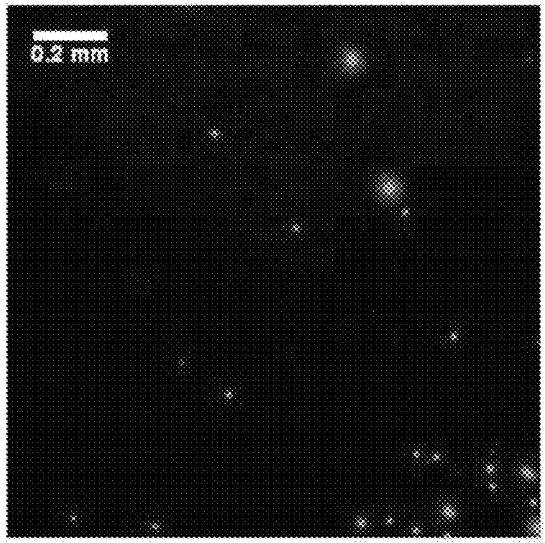
FIGS. 8A-8F. Optical images illustrating differences in drying pattern at the center (FIGS. 8A, 8B, 8C) and edge (FIGS. 8D, 8E, 8F) of a droplet containing i) red-fluorescent (Cy3) PS beads complementary to the 5' end of the EGFR amplicon, and ii) green-fluorescent (FITC) beads complementary to the 3' end on a glass surface when no EGFR amplicon is present. The images on the right (FIGS. 8C, 8F) are boolean AND combinations of the (FIGS. 8A, 8D) and (FIGS. 8B, 8E).
Figure 8B:
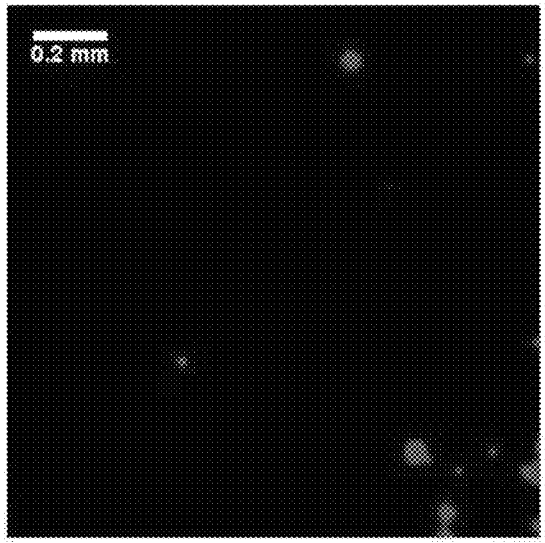
Figure 8C:
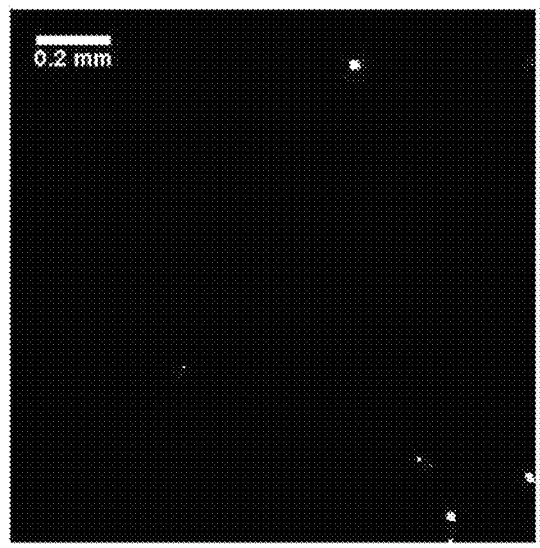
Figure 8D:
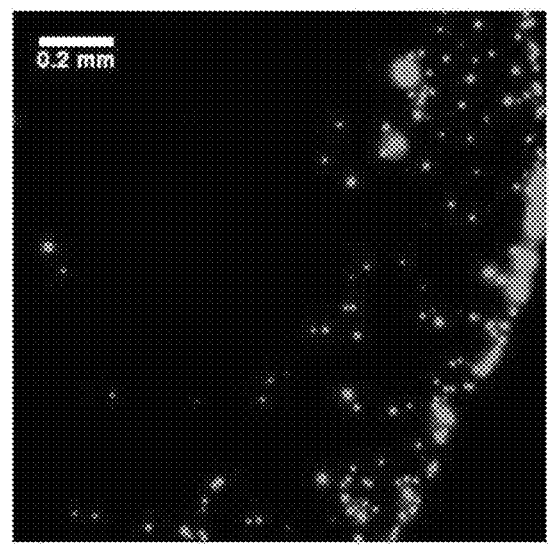
Figure 8E:
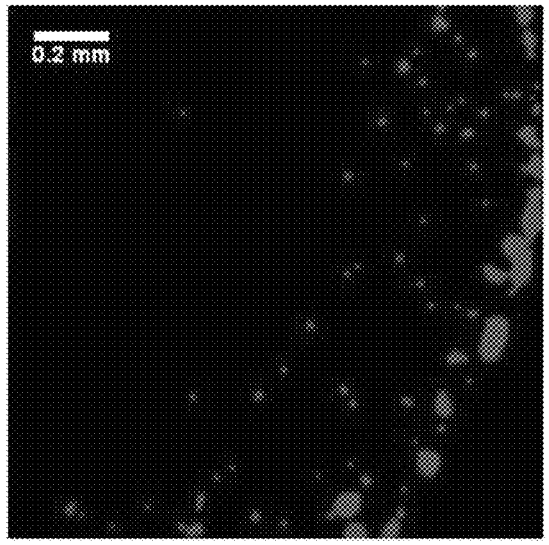
Figure 8F:
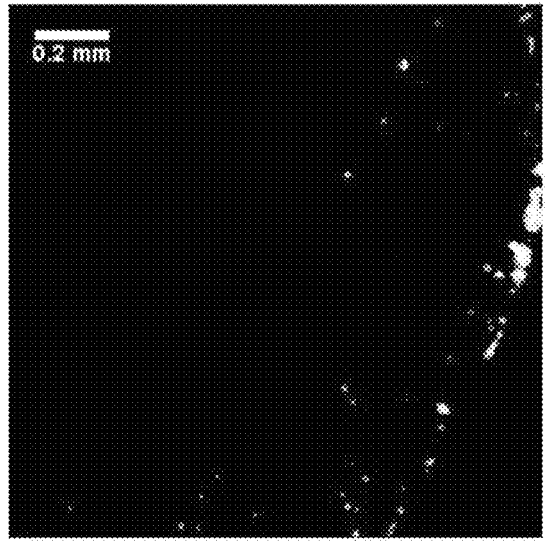

A first set of experiments involves direct interaction between one DNA fragment linked to the surface and another one on the bead in the presence or absence of the complementary DNA target, as well as in the presence of a complementary DNA target sequence with one mismatched base (SNP). For this, the streptavidin-coated surface was modified with a 3'-biotinylated oligonucleotide whereas the beads were modified with a 5'-biotinylated oligonucleotide (Table 1). Then, the target DNA was added as an allele-specific PCR amplicon after incubation while the glass surface was maintained at a temperature optimal for hybridization during the entire time needed for the droplet to dry on the surface (typically 100-130 seconds). The corresponding results are shown in FIGS. 7A-7G. In the first case (FIGS. 7A-7B), no EGFR target DNA is present and the "control" beads deposit mostly as a central bump with only a very small amount of beads outside this central area as judged by the fluorescent image. This situation is the expected normal evolution of a droplet containing particles with an average diameter of 0.5 µm given the temperature applied to the surface, as Marangoni recirculation from surface tension gradients will dominate radial flow [16,17]. When the A/A allele PCR-amplified DNA target is added to a final concentration around 30 pg/µL, the final distribution of the beads in the dried residue is very different from the "control" (FIGS. 7C-7D). The fluorescence image indeed shows that the beads deposit more uniformly when the A allele target is present as the interaction between the surface and the beads mediated by the target DNA is able to overcome the Marangoni recirculation and radial forces during the drying process. This situation is in agreement with the expectations from preliminary results using biotin-streptavidin [9] where the biological force between coated beads and the surface disturbs the expected drying mechanism of sub-microliter droplets. The situation using the G/G amplicon instead offers an intermediate state between the control and the A/A allele in terms of bead distribution in the droplet measured by fluorescence microscopy during the drying process (FIGS. 7E-7F). Most oligonucleotide-coated beads are still in the central region and the peripheral ring, but a closer examination shows the beads are more scattered around on the surface defined by the initial droplet imprint upon deposition on the surface. Such a situation is understandable as we expect less interaction between the beads and the surface given the SNP mismatch. The results from FIGS. 7A-7G support that when the EGFR SNP target is absent, the PS beads modified with a sequence complementary to the 5' end of the target simply slide onto the surface modified with a sequence complementary. But, when the EGFR target sequence is present, the beads and surface are linked by hybridization of the strands immobilized respectively on the bead and the surface to the respective sequence region on the EGFR amplicon. A mixed situation is obtained when the mismatched allele is dried on the surface showing the potential of our proposed method to detect SNP polymorphisms.

To further quantify the differences in the fluorescence signature of the residue of the different type of beads upon drying on the surface, we used radial distribution analysis and particle analysis with ImageJ (National Institutes of Health, Bethesda, Md.). FIG. 7G compares the average radial distribution frequency over 180° from the center of the image, i.e. the center of the initial deposition area. In the case of the control (no EGFR), over 90% of the fluorescence intensity (or beads) is contained within the first 100 µm value of radiuses (maximum: 188 µm), which reflects the presence of the beads in a central bump feature on the droplet residue. When the A/A allele, is present, the normalized radial distribution of the fluorescence intensity varies by only a few % around a central value of 20% all along the radius of the fluorescence image. This denotes a very uniform distribution of the fluorescence intensity, i.e. the beads, on the surface. When the G/G allele is present, the radial distribution profile shows an intermediate situation where about 80% of the intensity is obtained within the first 140 µm (out of 188 µm along a radius. This is less compact than for the control, but not as uniform as for the A/A allele experiment, which also suggests a weaker interaction—rather than no interaction—between the beads and the surface.

Surface-Independent Characterization

Figure 9A:
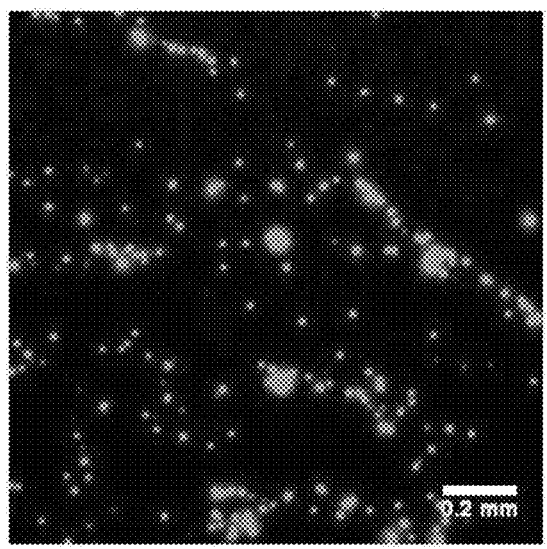
FIGS. 9A-9F. Differences in drying pattern at the center (FIGS. 9A, 9B, 9C) and edge (FIGS. 9D, 9E, 9F) of a droplet containing red-fluorescent (Cy3) PS beads complementary to the 5' end of the EGFR amplicon and green-fluorescent (FITC) beads complementary to the 3' end on a glass surface when the A/A allele is present at 58 pg/µL. The images on the right (FIGS. 9C, 9F) are boolean AND combinations of (FIGS. 9A, 9D) and (FIGS. 9B, 9E) and show locations where beads of each type are in close proximity. The presence of the EGFR amplicon increases the number of events in the boolean image indicating the presence of aggregates formed with each bead types, most likely bridged by the EGFR target.
Figure 9B:
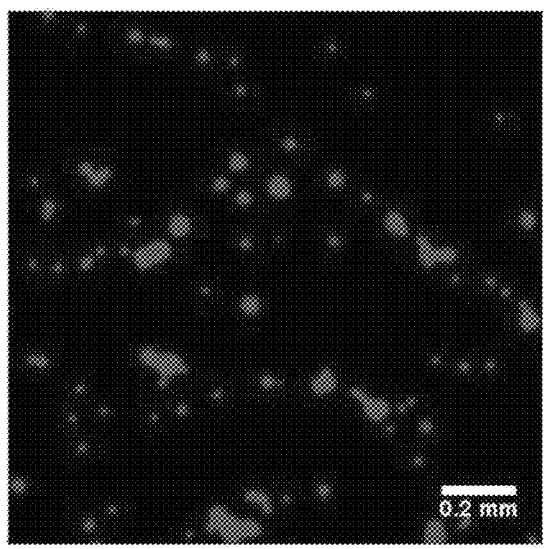
Figure 9C:
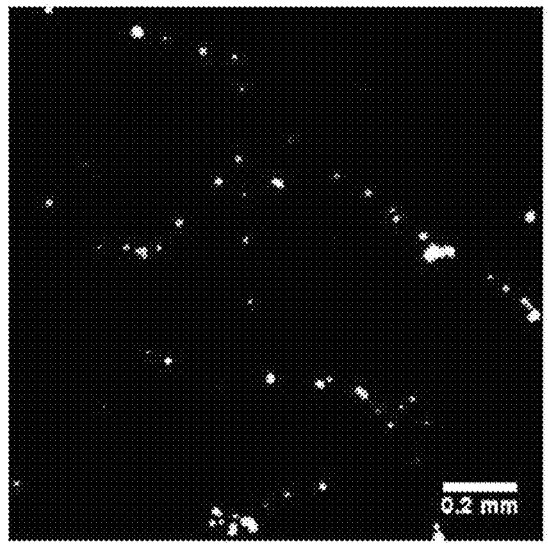
Figure 9D:
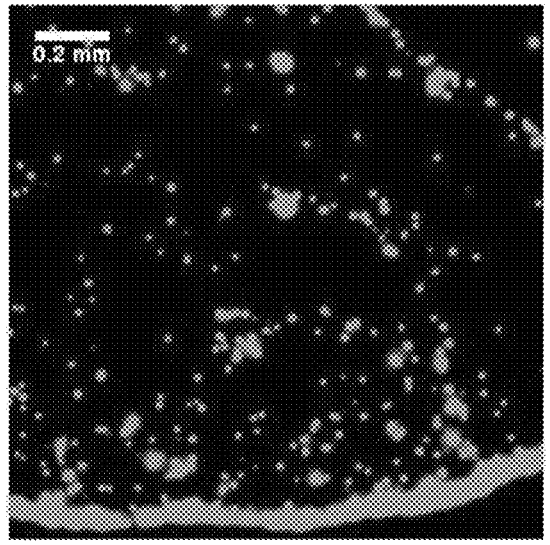
Figure 9E:
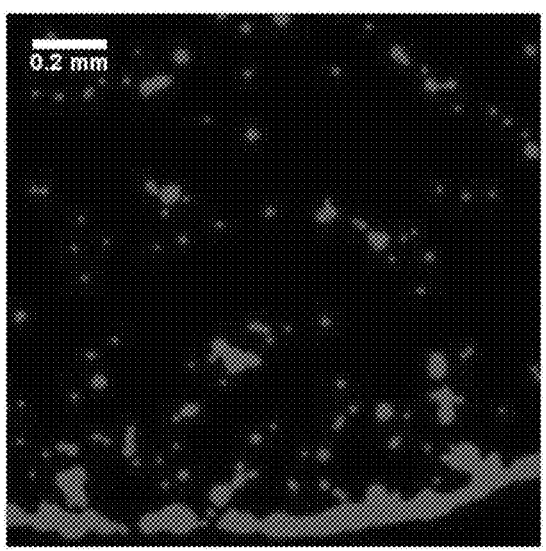
Figure 9F:
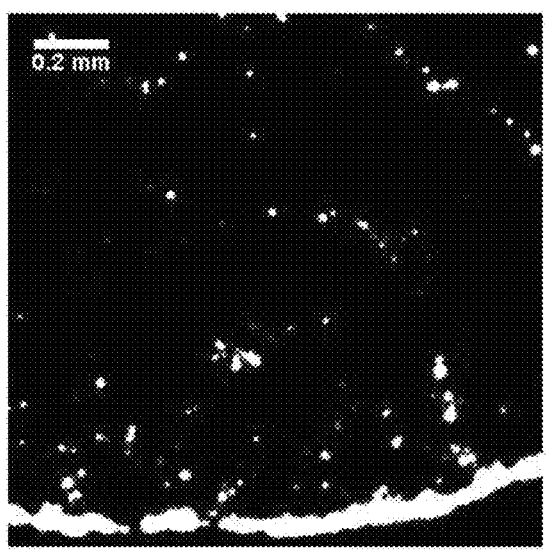

In the previous experimental approach, it is difficult to maintain the slide and the beads at temperatures above the $T_m$ of the oligonucleotides used to ensure efficient selective hybridization. To simplify the experimental protocol, a secondary characterization experiment was set up. A simple bare glass slide (Fisherbrand, cleaned with methanol) is used along with two types of beads: one coated with 3'-biotin-oligonucleotide with Nile Red fluorescent dye embedded in the hollow core, and another coated with the 5' biotin-oligonucleotide and Yellow dye embedded in the hollow core. Dual filter imaging (FITC and Cy3 filter sets) and image overlay was used to reveal the differences in the proximity of the two types of beads when EGFR is present or absent. Both the center and the edge of the droplet dried residue was systematically imaged (FIGS. 8A-8F). The absence of temperature gradients, since the slide is no longer heated, remove the dominance of Marangoni flow during the drying process and radial flow dominates [16], which is the reason why most droplet residue show a coffee-ring pattern where most beads are accumulated in the peripheral ring. However, in the control experiment (FIGS. 8A-8F, no EGFR amplicon present), the amount of beads present in the peripheral ring vs. those in the rest of the droplet residue is much higher than for the EGFR A/A allele (FIGS. 9A-9F). This is most likely because when beads of the two types are bridged into larger aggregates by the EGFR amplicon, the wetting line, given the drag force during the drying process, can no longer carry their increased weight and they tend to deposit onto the surface. In the presence of the EGFR A/A amplicon (FIGS. 9A-9F), there are clearly a much higher number of pixels in the Boolean AND combination of the FITC and Cy3 fluorescence images from each of the two types of beads used, especially in the central area of the droplet. Typically, less than 2% of pixels are positive in the Boolean image when no EGFR is present (FIGS. 8C, 8F) compared to over 20% when EGFR is present, with much larger areas (FIGS. 9C, 9F). This indicates a much higher occurrence of the close proximity of a beads emitting red fluorescence (observed with the Cy3 filter) and beads emitting green fluorescence (observed with the FITC filter) when the EGFR amplicon is present. Similarly, it suggests that the red beads and the green beads, each modified with a complement sequence to opposite regions of the EGFR amplicon, are located much closer to each other and occasionally aggregated in the sample containing the EGFR A/A amplicon than in the control where no sample is present. The results from FIGS. 8A-8F and 9A-9F corroborate those of FIGS. 7A-7G, but with a simplified experimental setup that does not require a modified glass slide maintained at a precisely controlled temperature. In each type of experiment, we show clear evidence that the presence of the target EGFR DNA strongly modifies the behavior of the microdroplet upon unforced drying in ambient atmosphere.

With added quantification using pattern recognition algorithms for automated image analysis, our observations can lead to a rapid diagnosis method for the presence of a short (<60 base pairs) SNP DNA target relevant to a particular disease, similarly to the presented model with a registered EGFR SNP. Efforts are now focused on determining the limit of detection. In the reported results, the final DNA concentration from dilution of the PCR amplicons is around 40 pg/µL, which would correspond to a limited number of PCR amplification cycles [18]. Therefore, any of the methods provided herein optionally comprise target amplification prior to detection.

In line with our observations of how biotin beads modify the drying mechanism of microdroplets on streptavidin-coated slides, we present results, using two alternative experimental characterization methods, on how specific DNA hybridization can be detected using similar changes to the final dried residue of microdroplets containing similar beads modified with specific DNA sequences. We chose a model system of a well-known SNP of the EGFR protein involved in several devastating cancers, but our results merely illustrate how the proposed method can be applied to rapid imaging-based diagnosis of a multitude of biomarkers. We analyze fluorescence microscopy data to show how the final distribution of fluorescent beads—modified with a complementary sequence to the 5' end of the EGFR DNA target—is affected by the presence of the target using either a glass surface, or a second set of fluorescent beads modified with a sequence complementary to the 3' end of the EGFR DNA target. A first experimental method using a chemically modified glass slide maintained at a control temperature close to the melting temperatures, $T_m$, of the DNA fragments used provides a simple image analysis, but requires a more complex experimental setup while the second method requires dual fluorescence channel imaging but uses a simple glass slide at room temperature. In each case, we provide clear evidence of the detection of the EGFR target DNA at a final concentration around 40 pg/µL. Our results support biomedical diagnostic methods for handheld portable point-of-care (POC) devices. All the more so as our experimental strategy can be adapted to immunoassays instead of DNA hybridization for protein detection as well by immobilizing antibodies rather than DNA oligonucleotides. Multiplexing assays for low cost arrays are of particular interest.

REFERENCES

1. Sangani A. S., Lu C. H., Su K. H., Schwarz J. A., *Phys. Rev. E,* 80, 011603 (2009).
2. Thiele U., *Adv. Colloid Interface Sci.,* 206, 399 (2014).
3. Sefiane K, Bennacer R., *Adv. Colloid Interface Sci.,* 147-148, 263 (2009).
4. Baughman K. F., Maier R. M., Norris T. A., Beam B. M., Mudalige A, Pemberton J. E., Curry J. E., *Langmuir,* 26, 7293 (2010).
5. Xu W, Leeladhar R, Tsai Y. T., Yang E. H., Choi C. H., *Appl. Phys. Lett.,* 98, 073101 (2011).
6. Accardo A, Gentile F, Mecarini F, De Angelis F, Burghammer M, Di Fabrizio E, Riekel C., *Microelectron. Eng.,* 88, 1660 (2011).
7. Lee C. Y., Zhang B. J., Park J, Kim K. J., *Int. J. Heat Mass Transf.,* 55, 2151 (2012).
8. Ristenpart W. D., Kim P. G., Domingues C, Wan J, Stone H. A., *Phys. Rev. Lett.,* 99, 234502 (2007).
9. Hurth C, Bhardwaj R, Andalib S, Frankiewicz C, Dobos A, Attinger D, Zenhausern F., *Chem. Eng. Sci.,* 137, 398 (2015).
10. Trantum J. R., Wright D. W., Haselton F. R., *Langmuir,* 28, 2187 (2012).
11. Kim N, Li Z, Hurth C, Zenhausern F, Chang S. F., Attinger D., *Anal. Methods,* 4, 50 (2012).
12. Holmberg A, Nord O, Lukacs M, Lundesberg J, Uhlén M., *Electrophoresis,* 26, 501 (2005).
13. Wong T, Chilkoti A, Moy V T., *Biomol. Eng.,* 16, 45 (1999).
14. Howley P. M., Israel M. F., Law M. F., Martin M. A., *J. Biol. Chem.,* 254, 4876 (1979).
15. Dressman D, Yan H, Traverso G, Kinzler K. W., Vogelstein B., *Proc. Nat. Acad. Sci. USA,* 100, 8817 (2003).
16. Bhardwaj R, Fang X, Somasundaran P, Attinger D., *Langmuir,* 26, 7833 (2010).
17. Hu H., Larson R. G., *Langmuir,* 21, 3972 (2005).
18. Lin C. C., Huang W. L., Wei F, Su W. C., Wong D. T., *Expert Rev Mol Diagn.,* 15, 1427 (2015).

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a length range, temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

TABLES

TABLE 1

Context sequence and synthetic oligonucleotides designed for the sensing of rs1050171 EGFR SNP. (*) calculated at 250 pM in 180 mM Na⁺ equivalent and at 25° C.

| rs1050171 | Base Sequence | $T_m$ (° C.)* | $\Delta G_{int}$* (kcal/mole) |
|---|---|---|---|
| Context sequence (SEQ ID NO: 1) | GCA TCT GCC TCA CCT CCA CCG TGC A[A/G]C TCA TCA CGC AGC TCA TGC CCT TCG | 95.6 | n/a |
| Complementary strand (SEQ ID NO: 2) | CGA AGG GCA TGA GCT GCG TGA TGA G[T/C]T GCA CGG TGG AGG TGA GGC AGA TGC | n/a | n/a |
| Surface-coupled oligo. (SEQ ID NO: 3)-Biotin | CGG TGG AGG TGA GGC AGA TGC AAA-Biotin | 74.0 | −43.66 |
| Type 1 bead-coupled oligo. (T allele) Biotin-(SEQ ID NO: 4) | Biotin-AAA AAA CGA AGG GCA TGA GCT GCG TGA TGA GTT GCA | 83.0 | −62.81 |
| Type 2 bead-coupled oligo. (G mismatch) Biotin-(SEQ ID NO: 5) | Biotin-AAA AAA CGA AGG GCA TGA GCT GCG TGA TGA GGT GCA | 84.2 | −10.54 |

TABLE 2

Droplet solutions arrayed in replicates on the surface modified with 3' biotinylated oligonucleotides for a given bead dilution, EGFR amplicon concentration.

| Type | Content | Purpose |
|---|---|---|
| 1 | 1:500 dilution native SAv-coated beads in binding buffer* buffer incubated with EGFR A/A amplicon at T > Tm for 1-2 h. | Negative control for false positives from interaction between SAv-coated beads and biotin labels from oligonucleotides on surface |
| 2 | 1:500 dilution SAv-coated/5'-biotinylated oligonucleotides in binding buffer | Negative control for false positives from non-specific hybridization (cross dimers) between biotinylated oligonucleotides |
| 3 | 1:500 dilution SAv-coated/5'-biotinylated oligonucleotides in building buffer incubated with EGFR A/A amplicon at T > Tm for 1-2 h. | Sample 1. Sense detection efficiency of a dilute pure A/A PCR amplicon |
| 4 | 1:500 dilution SAv-coated/5'-biotinylated oligonucleotides in binding buffer incubated with EGFR G/G amplicon at T > Tm for 1-2 h. | Sample 2. Sense detection efficiency of a dilute pure G/G PCR amplicon and test SNP recognition capabilities |
| 5 | ≈10 μM dilution 5'-FAM-labeled biotinylated oligonucleotides in binding buffer incubated with EGFR A/A amplicon at T > Tm for 1-2 h. | Positive control for false negative from loss of biotinylated oligonucleotide from the bead surface |

*Binding buffer: 10 mM Tris, 1 mM EDTA, 2M NaCl, pH = 8.0.

TABLE 3

Prepared solutions arrayed on the streptavidin glass slide coated with the 3'-biotin-oligonucleotides. An additional 1:2000 dilution was performed in buffer to allow observation using fluorescence microscopy.

| Solution Name | Base Content | Target Content |
|---|---|---|
| CONTROL | 50 μL PS beads bound with 5'-biotin-oligonucleotides | None |
| SAMPLE A | 50 μL PS beads bound with 5'-biotin-oligonucleotides | 1 μL A/A amplicon (stock: 1-2 ng/μL) |
| SAMPLE G | 50 μL PS beads bound with 5'-biotin-oligonucleotides | 1 μL G/G amplicon (stock: 2-3 ng/μL) |

We claim:

1. A method of retrieving digital information stored in a biological system, the method comprising the steps of:
   translating digital information to a biomolecular medium;
   providing a microarray comprising a substrate receiving surface and a plurality of unique substrate-bound sequences in a selected pattern;
   depositing a liquid droplet, or an array of liquid droplets, to the substrate receiving surface, wherein the liquid droplet comprises the biomolecular medium;
   drying the liquid droplet(s) on the substrate receiving surface to form a progressive recession of a wetting line corresponding to a biological information pattern (BIP) wetting line and a corresponding dried residue pattern, wherein the recession of the BIP wetting line and corresponding dried residue pattern is influenced by an interaction or a lack of interaction between the biomolecular medium and the plurality of unique substrate-bound sequences to form a BIP;
   imaging the dried residue pattern with an imager; and
   processing the image of the dried residue pattern with a processer to calculate a wetting line optical parameter from the BIP wetting line, thereby decoding digital information stored in the biomolecular medium.

2. The method of claim 1, wherein the biomolecular medium comprises a nucleic acid molecule.

3. The method of claim 1, that is label-free.

4. The method of claim 1, wherein the imaging step is by a sensor in a hand-held or mobile device.

5. The method of claim 1, wherein the biomolecular medium comprises three regions:
   a bead-binding sequence region;
   a substrate-binding sequence region; and
   a digital information region positioned between the bead-binding and substrate-binding regions.

6. The method of claim 1, wherein the biomolecular medium comprises a nucleic acid sequence, an amino acid sequence, or a combination thereof and the substrate-bound sequences correspondingly comprise a nucleic acid sequence, an amino acid sequence, or a combination thereof.

7. The method of claim 6, wherein the biomolecular medium comprises a plurality of short-stranded ssDNA, optionally of a length of between 20 and 50 nucleotides.

8. The method of claim 1, wherein the liquid droplet(s) further comprise beads having a bead surface and a plurality of bead-bound sequences connected to the bead surface, wherein the bead-bound sequences have a sequence-binding region configured to bind to a bead-binding sequence region of a target sequence.

9. The method of claim 8, wherein the beads comprise a polystyrene bead library.

10. A biological information pattern (BIP) system for readout of digital information stored in a biological medium comprising:
    a microarray having:
      a substrate with a receiving surface;
      a plurality of unique substrate-bound sequences, each having a unique target sequence binding region;
    a liquid droplet or an array of liquid droplets deposited on said substrate receiving surface, wherein said liquid droplet comprises beads and contains digital information stored in a biomolecular medium and said biomolecular medium comprises:
      a plurality of target sequences, each target sequence having a target substrate-binding sequence region, a target bead-binding sequence region, and an information region positioned between the target substrate-binding sequence region and the target bead-binding sequence region;
    an imager to detect the BIP;
    wherein the target sequence binding region of the substrate-bound sequences are configured to specifically bind to the target substrate binding sequence region of a target sequence;
    wherein during use said liquid droplet and plurality of unique substrate-bound sequences form a BIP wetting line detected by said imager to provide a read-out of the digital information;
    wherein the imager comprises a camera to optically detect the BIP wetting line; and
    a processor configured to calculate a wetting line optical parameter from the BIP wetting line.

11. The BIP system of claim 10, wherein the wetting line optical parameter is one or more of: a geometric shape, a size, or a location on the substrate receiving surface.

12. The BIP system of claim 11, wherein a readout of digital information is a label-free readout of a specific dried residue pattern.

13. The BIP system claim 10, further comprising: a plurality of beads in the liquid medium, wherein the beads have a bead surface and a plurality of bead-bound sequences connected to the bead surface, wherein the bead-bound sequences have a target sequence-binding region configured to specifically bind to a bead-binding target sequence region of the target sequence.

14. The BIP system of claim 10, wherein the sequences comprise nucleotide sequences.

* * * * *

SEQUENCE LISTING

```
<160> NUMBER OF SEQ ID NOS: 5

<210> SEQ ID NO 1
<211> LENGTH: 51
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (26)..(26)
<223> OTHER INFORMATION: n is A or G

<400> SEQUENCE: 1
gcatctgcct cacctccacc gtgcanctca tcacgcagct catgcccttc g          51

<210> SEQ ID NO 2
<211> LENGTH: 51
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (26)..(26)
<223> OTHER INFORMATION: n is T or C

<400> SEQUENCE: 2
cgaagggcat gagctgcgtg atgagntgca cggtggaggt gaggcagatg c          51

<210> SEQ ID NO 3
<211> LENGTH: 24
<212> TYPE: DNA
<213> ORGANISM: Artificial Sequence
<220> FEATURE:
<223> OTHER INFORMATION: Synthetic Construct

<400> SEQUENCE: 3
cggtggaggt gaggcagatg caaa                                         24

<210> SEQ ID NO 4
<211> LENGTH: 36
<212> TYPE: DNA
<213> ORGANISM: Artificial Sequence
<220> FEATURE:
<223> OTHER INFORMATION: Synthetic Construct

<400> SEQUENCE: 4
aaaaaacgaa gggcatgagc tgcgtgatga gttgca                            36

<210> SEQ ID NO 5
<211> LENGTH: 36
<212> TYPE: DNA
```

```
<213> ORGANISM: Artificial Sequence
<220> FEATURE:
<223> OTHER INFORMATION: Synthetic Construct

<400> SEQUENCE: 5
aaaaaacgaa gggcatgagc tgcgtgatga ggtgca                              36
```